United States Patent
Egan

(10) Patent No.: US 11,446,021 B2
(45) Date of Patent: Sep. 20, 2022

(54) ELECTRICALLY WELDABLE SUTURE MATERIAL, AND APPARATUS AND METHOD FOR FORMING WELDED SUTURE LOOPS AND OTHER WELDED STRUCTURES

(71) Applicant: Egan Design LLC, Marblehead, MA (US)

(72) Inventor: Thomas D. Egan, Marblehead, MA (US)

(73) Assignee: Egan Design LLC, Marblehead, MA (US)

( * ) Notice: Subject to any disclaimer, the term of this patent is extended or adjusted under 35 U.S.C. 154(b) by 475 days.

(21) Appl. No.: 16/190,915

(22) Filed: Nov. 14, 2018

(65) Prior Publication Data
US 2019/0142419 A1 May 16, 2019

Related U.S. Application Data

(60) Provisional application No. 62/586,108, filed on Nov. 14, 2017.

(51) Int. Cl.
*A61B 17/06* (2006.01)
*B29C 65/04* (2006.01)
(Continued)

(52) U.S. Cl.
CPC .... *A61B 17/06166* (2013.01); *A61B 17/0469* (2013.01); *A61B 17/0487* (2013.01);
(Continued)

(58) Field of Classification Search
CPC .......... A61B 17/06166; A61B 17/0469; A61B 17/0487; A61B 17/0401; A61B 17/68;
(Continued)

(56) References Cited

U.S. PATENT DOCUMENTS 3,657,056 A * 4/1972 Winston .................. A61B 17/04
156/580.2
4,662,068 A * 5/1987 Polonsky ............... A61B 17/04
30/124
(Continued)

FOREIGN PATENT DOCUMENTS

EP 1 009 288 6/2000
EP 2 075 012 7/2009
(Continued)

OTHER PUBLICATIONS

International Search Report and Written Opinion of the International Searching Authority issued in connection with International (PCT) Patent Application No. PCT/US18/61043, dated Mar. 15, 2019.
(Continued)

*Primary Examiner* — Katherine H Schwiker
(74) *Attorney, Agent, or Firm* — Jones Robb, PLLC

(57) ABSTRACT

A device for positioning in the body of an animal, the device comprising a first portion and a second portion that may be positioned in contact with one other, the first portion and the second portion each comprising a biocompatible conductive thermoplastic material, such that when the device is positioned in the body of an animal and electric current flows from the first portion to the second portion, heat is generated by electrical resistance at the point of contact between the first portion and the second portion so as to melt regions of the first portion and the second portion, and when the electric current is thereafter terminated, the melted regions of the first portion and the second portion re-solidify so that a weld is formed between the first portion and the second portion.

22 Claims, 15 Drawing Sheets

(51) Int. Cl.
    *A61B 17/04*        (2006.01)
    *A61L 17/00*        (2006.01)
    *A61L 17/06*        (2006.01)
    *A61L 17/14*        (2006.01)
    *B29C 65/34*       (2006.01)
    *B29C 65/00*       (2006.01)
    *B29C 65/74*       (2006.01)
    *A61B 17/064*      (2006.01)
    *A61B 17/122*      (2006.01)
    *A61B 34/00*       (2016.01)
    *B29K 505/00*      (2006.01)
    *B29L 31/00*       (2006.01)
    *B29K 105/16*      (2006.01)
    *A61B 17/00*       (2006.01)
    *B29K 507/04*      (2006.01)

(52) U.S. Cl.
CPC ........ *A61B 17/0643* (2013.01); *A61B 17/122* (2013.01); *A61L 17/005* (2013.01); *A61L 17/06* (2013.01); *A61L 17/14* (2013.01); *B29C 65/04* (2013.01); *B29C 65/3412* (2013.01); *B29C 65/3416* (2013.01); *B29C 65/3468* (2013.01); *B29C 65/7451* (2013.01); *B29C 66/112* (2013.01); *B29C 66/114* (2013.01); *B29C 66/1122* (2013.01); *B29C 66/30221* (2013.01); *B29C 66/50* (2013.01); *B29C 66/5346* (2013.01); *B29C 66/69* (2013.01); *B29C 66/73141* (2013.01); *B29C 66/73921* (2013.01); *B29C 66/8161* (2013.01); *B29C 66/832* (2013.01); *B29C 66/863* (2013.01); *B29C 66/8618* (2013.01); *A61B 17/0483* (2013.01); *A61B 34/00* (2016.02); *A61B 2017/00955* (2013.01); *A61B 2017/0608* (2013.01); *A61B 2017/0619* (2013.01); *B29C 65/3476* (2013.01); *B29C 65/3492* (2013.01); *B29C 66/71* (2013.01); *B29C 66/7212* (2013.01); *B29C 66/72143* (2013.01); *B29K 2105/162* (2013.01); *B29K 2505/00* (2013.01); *B29K 2507/04* (2013.01); *B29L 2031/709* (2013.01); *B29L 2031/753* (2013.01)

(58) Field of Classification Search
CPC ... A61B 17/06195; A61B 2017/06171–06185; A61L 17/06; B29C 65/04
See application file for complete search history.

(56) References Cited

U.S. PATENT DOCUMENTS

| | | | |
|---|---|---|---|
| 5,133,727 A | | 7/1992 | Bales et al. |
| 5,417,700 A | * | 5/1995 | Egan ................ A61B 17/0469 |
| | | | 606/144 |
| 5,618,290 A | | 4/1997 | Frederick et al. |
| 5,766,186 A | | 6/1998 | Feraz et al. |
| 5,893,880 A | * | 4/1999 | Egan ................... B29C 66/1122 |
| | | | 606/228 |
| 6,358,271 B1 | | 3/2002 | Egan et al. |
| 6,793,750 B2 | | 9/2004 | Bittar |
| 7,090,111 B2 | | 8/2006 | Egan et al. |
| 9,017,346 B2 | | 4/2015 | Kia et al. |
| 10,245,023 B2 | | 4/2019 | Kia et al. |
| 2002/0035371 A1 | | 3/2002 | Westhaver et al. |
| 2002/0188304 A1 | | 12/2002 | Mollenauer et al. |
| 2003/0014077 A1 | * | 1/2003 | Leung .............. A61B 17/06166 |
| | | | 606/228 |
| 2003/0050649 A1 | | 3/2003 | Brock et al. |
| 2004/0172107 A1 | | 9/2004 | Fox |
| 2005/0048859 A1 | * | 3/2005 | Canham ........... A61B 17/06166 |
| | | | 442/189 |
| 2006/0265042 A1 | * | 11/2006 | Catanese ............ A61B 17/0625 |
| | | | 623/1.11 |
| 2007/0134292 A1 | | 6/2007 | Suokas et al. |
| 2008/0039845 A1 | | 2/2008 | Bonutti et al. |
| 2008/0086152 A1 | * | 4/2008 | McKay .............. A61B 17/0469 |
| | | | 606/139 |
| 2009/0012538 A1 | | 1/2009 | Saliman et al. |
| 2009/0062851 A1 | | 3/2009 | Rosenblatt |
| 2009/0259251 A1 | | 3/2009 | Cohen |
| 2009/0131979 A1 | * | 5/2009 | Thompson ........ A61B 17/06166 |
| | | | 606/224 |
| 2010/0241229 A1 | * | 9/2010 | Baehre ................. A61B 17/122 |
| | | | 623/16.11 |
| 2011/0313433 A1 | | 12/2011 | Woodard et al. |
| 2013/0092719 A1 | | 4/2013 | Kostrzewski |
| 2013/0150842 A1 | | 6/2013 | Nau, Jr. et al. |
| 2013/0253533 A1 | | 9/2013 | Bartol |
| 2014/0097554 A1 | | 4/2014 | Fenton et al. |
| 2014/0276778 A1 | * | 9/2014 | McLawhorn ....... A61B 18/1492 |
| | | | 606/41 |
| 2015/0099959 A1 | | 4/2015 | Bonmassar et al. |
| 2016/0022332 A1 | | 1/2016 | Baehre et al. |
| 2016/0338691 A1 | | 11/2016 | Weber et al. |
| 2016/0345563 A1 | | 12/2016 | Fenton et al. |
| 2018/0228486 A1 | | 8/2018 | Ravikumar et al. |

FOREIGN PATENT DOCUMENTS

| | | |
|---|---|---|
| WO | WO2012/006491 | 12/2012 |
| WO | WO2017/039677 | 9/2017 |

OTHER PUBLICATIONS

International Search Report and Written Opinion of the International Searching Authority issued in connection with International (PCT) Patent Application No. PCT/US20/17167, dated Jun. 16, 2020.

* cited by examiner (Detail view with section outline)

ELECTRICALLY WELDABLE SUTURE MATERIAL, AND APPARATUS AND METHOD FOR FORMING WELDED SUTURE LOOPS AND OTHER WELDED STRUCTURES

REFERENCE TO PENDING PRIOR PATENT APPLICATION

This patent application claims benefit of prior U.S. Provisional Patent Application Ser. No. 62/586,108, filed Nov. 14, 2017 by Thomas Egan for ELECTRICALLY WELDABLE SUTURE MATERIAL, APPARATUS AND PROCESS FOR FORMING WELDED SUTURE LOOPS AND OTHER STRUCTURES, which patent application is hereby incorporated herein by reference.

FIELD OF THE INVENTION

This invention relates to the use of electrical energy to fuse polymer materials into useful shapes, and more particularly to the use of electrical energy to fuse polymer materials into useful shapes in the body of an animal (which term is intended to include humans and other mammals), and even more particularly to the use of electrical energy to fuse polymer sutures and other structures for the surgical joining of tissues in a body such as for surgical suturing and vessel or organ closure.

BACKGROUND OF THE INVENTION

In surgical procedures, a suture is typically used to secure the edges of tissue together so as to maintain those tissue edges in proximity to one another until healing is substantially completed. The suture is generally directed through the portions of the tissue to be joined and formed into a single loop or stitch, which is then knotted or otherwise secured (e.g., with a crimped fastener) so as to maintain the edges of the tissue in the appropriate relationship to each other for healing to occur.

In some situations a series of individual, separate stitches of substantially uniform tension are made in tissue. Inasmuch as the stitches are individual and separate from one another, the removal of one stitch does not require the removal of all of the stitches or cause the remaining stitches to loosen. However, each individual stitch requires an individual knot (or some other stitch-closing device, e.g., a crimped fastener) for securing the stitch in place about the wound.

It is sometimes necessary or desirable to close a wound with sutures without having to form knots in the suture or utilize loop-closing devices (e.g., crimped fasteners), such as, for example, in the surgical repair of organs or tissues where access to the repair site is restricted. In these situations, a fused loop of suture can be used to maintain the wound edges in sufficient proximity for a sufficient period of time to allow healing to occur.

Polymer sutures are particularly amenable to various fusing or joining processes, such as, for example, by welding, where sections of the sutures can be fused together upon application of sufficient heat to the sections to cause partial melting and fusion of the sections of the sutures.

Efforts have heretofore been made to fuse together segments of polymer suture using (i) the direct application of heat, or (ii) the application of ultrasonic energy.

Unfortunately, effecting welding via the direct application of heat suffers from two significant disadvantages. First, the direct application of heat to sutures in situ may produce undesirable heating of the surrounding tissue. Second, with the direct application of heat to sutures, it is difficult to selectively melt only the interface between the suture segments which are to be welded without melting the entire cross-section of the suture, which can drastically weaken the suture.

For these reasons, it is generally preferred to apply non-thermal energy to the suture material in situ in order to induce localized heating of the suture material in the areas or sections to be fused. In particular, ultrasonic energy may be effectively applied to sections of suture material to induce frictional heating of the sections in order to fuse or weld the sections of the suture together. While such ultrasonic welding of sutures can be an important improvement over direct thermal welding of sutures (i.e., ultrasonic welding melts only the parts of the suture that touch each other and not the whole cross-section of the suture), thereby preserving the strength of the suture, ultrasonic welding suffers from two significant disadvantages of its own. First, ultrasonic welding requires bulky, expensive equipment. Such equipment may not be compatible with certain kinds of surgery and, in any case, increases cost. Second, due to the nature of ultrasonic transducers and waveguides, ultrasonic welding requires straight line access between the energy source and the weld site, so that it is incompatible with curved or flexible instruments.

It is, therefore, an object of the present invention to provide a new and improved approach for forming connections (which may also be referred to as joinders or welds) within the body which does not suffer from the problems associated with the prior art.

SUMMARY OF THE INVENTION

The present invention comprises the provision and use of a new and improved approach for forming connections (which may also be referred to as joinders or welds) within the body which does not suffer from the problems associated with the prior art.

Among other things, the present invention comprises the provision and use of a new and improved method and apparatus for producing suture welds of sufficient strength and reliability to replace suture knots or other loop-closure devices.

One important aspect of the present invention comprises the provision and use of a new kind of polymer biomaterial that is strong, biologically compatible, and weldable with electrical energy (i.e., "an electrically weldable polymer").

Another important aspect of the present invention is the provision and use of a method for joining polymer devices in a body to make medically useful structures.

And another important aspect of the present invention is the provision and use of apparatus for delivering and joining medically useful structures in a body.

Still another important aspect of the present invention is the provision and use of novel medically useful structures, including, but not limited to, (i) a fused loop of electrically weldable polymer; (ii) a welded hemostasis clip of electrically weldable polymer; and (iii) a continuously deliverable, staple-like chain of electrically weldable polymer fasteners.

In one form of the present invention, there is provided a device for positioning in the body of an animal, the device comprising a first portion and a second portion that may be positioned in contact with one other, said first portion and said second portion each comprising a biocompatible conductive thermoplastic material, such that when the device is positioned in the body of an animal and electric current flows from said first portion to said second portion, heat is generated by electrical resistance at the point of contact between said first portion and said second portion so as to melt regions of said first portion and said second portion, and when the electric current is thereafter terminated, the melted regions of said first portion and said second portion re-solidify so that a weld is formed between said first portion and said second portion.

In another form of the present invention, there is provided apparatus for forming a weld between a first portion of a biocompatible conductive thermoplastic material and a second portion of a biocompatible conductive thermoplastic material, the apparatus comprising:

a first electrode;

a second electrode;

a structure for holding said first and second electrodes in opposition to one other with a space therebetween for receiving said first portion and said second portion in contact with one another, wherein said structure is non-conductive of electricity; and an electrical circuit comprising a power source and a switch arranged such that closure of said switch applies a voltage potential across said first electrode and said second electrode, such that when said first and second portions are positioned in the body of an animal and placed between said first and second electrodes in contact with one another and said switch is thereafter closed, heat is generated by electric resistance at the point of contact so as to melt regions of said first and second portions, and when said switch is thereafter opened, the melted portions of said first and second portions re-solidify so that a weld is formed at the point of contact.

In another form of the present invention, there is provided a method for forming a weld between two portions of a biocompatible conductive thermoplastic material in the body of an animal, wherein the method comprises:

positioning first and second portions of a biocompatible conductive thermoplastic material in the body of an animal between first and second electrodes so that said first portion is in contact with said first electrode, said second portion is in contact with said second electrode, and said first and second portions of the biocompatible conductive thermoplastic material are in contact with one another;

applying a selected amount of electrical current across said first and second electrodes so as generate a selected amount of heat by electric resistance at the point of contact between said first and second portions so as to cause a specific desired amount of melting of said first and second portions; and terminating the electrical current across said first and second electrodes so that the melted regions of said first and second portions re-solidify so that a weld is formed at the point of contact.

In another form of the present invention, there is provided an end effector for a suturing device, the end effector comprising:

a first arm having a tissue-engaging surface;

a second arm having a tissue-engaging surface;

at least one of said first and second arms being configured for movement (i) toward the other of said first and second arms so as to clamp tissue between said tissue-engaging surface of said first arm and said tissue-engaging surface of said second arm, and (ii) away from the other of said first and second arms so as to release tissue clamped between said tissue-engaging surface of said first arm and said tissue-engaging surface of said second arm;

said second arm having an opening therein; and a needle having a penetrating tip, said needle being configured for movement (i) toward said tissue-engaging surface of said first arm so as to position said penetrating tip of said needle adjacent to said tissue-engaging surface of said first arm, whereby to penetrate tissue clamped between said tissue-engaging surface of said first arm and said tissue-engaging surface of said second arm, and (ii) away from said tissue-engaging surface of said first arm so as to withdraw from tissue clamped between said tissue-engaging surface of said first arm and said tissue-engaging surface of said second arm;

said needle being configured to pass through said opening in said second arm as said needle moves toward said tissue-engaging surface of said first arm and to pass through said opening in said second arm as said needle moves away from said tissue-engaging surface of said first arm.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
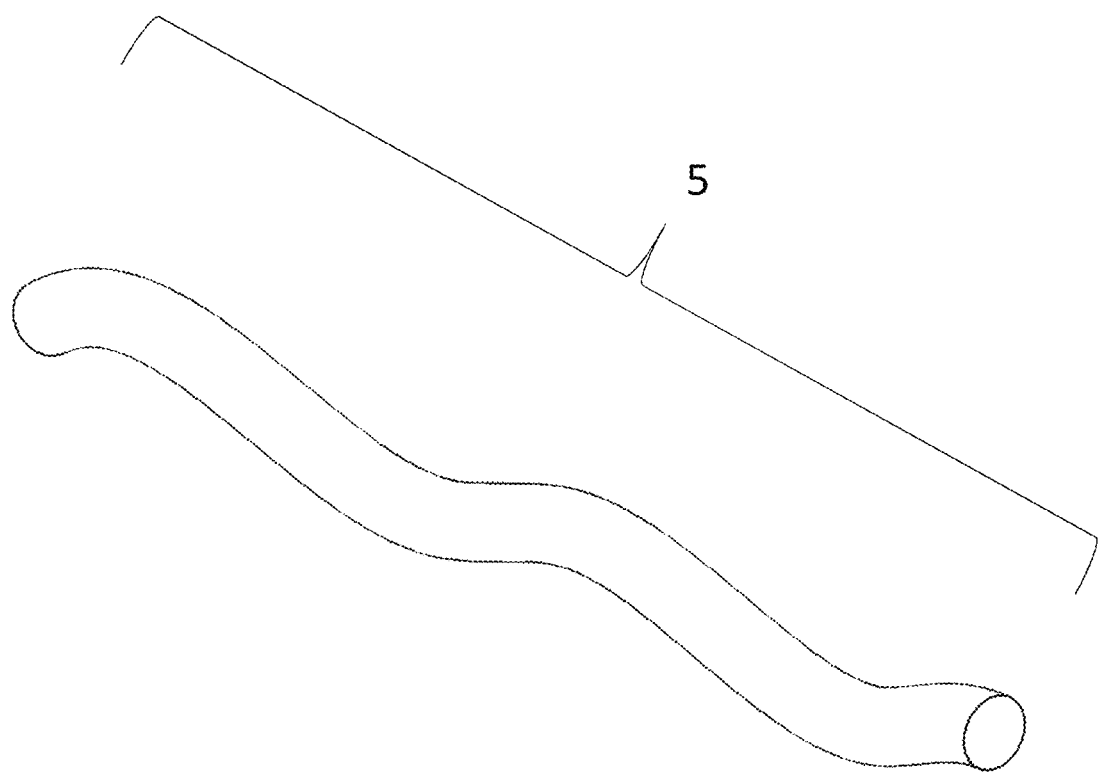
FIG. 1 is a schematic view showing a short length of filamentous material formed in accordance with the present invention (the filamentous material is sometimes referred to herein as "conductive thermoplastic suture")

The present invention comprises the provision and use of a new and improved method and apparatus for producing suture welds of sufficient strength and reliability to replace, or enhance the strength of, suture knots or other loop closure devices.

This disclosure describes inventive concepts with reference to specific examples. However, the intent is to cover all modifications, equivalents, and alternatives of the inventive concepts that are consistent with this disclosure.

The Invention in General

Forming surgical stitches in anatomic regions with difficult surgical access is a challenge in minimally invasive surgery. This disclosure describes an invention that joins sutures by welding (instead of, for example, tying or knotting). This saves time and can be done in extremely confined spaces. Unlike existing suture welding systems, the present invention can deliver suture welds through a serpentine path, such as through a curved catheter, using low-cost welding apparatus. Aspects of the disclosed invention can be particularly beneficial to manufacturers of robotic surgical systems. For example, a fully automated suturing device accessory can be utilized in surgical robotic systems.

Conventional "needle-and-thread" suturing requires manual or instrument access and is time-consuming, requires maneuvering room and leaves bulky knots at the surgical site. Crimp-type joinder devices leave behind a foreign body (e.g., a metal crimp) at the joinder site, and the high crimping force required to actuate the crimp necessitates substantial shaft diameter and limited shaft length. Existing suture welding devices utilizing the direct application of heat risk undesirable heating of surrounding tissues and/or suture weakening. Existing ultrasonic suture welding devices are bulky and expensive and require straight line access to the surgical site. Existing surgical robotic manipulators are time-consuming, require maneuvering room, and have a steep learning curve.

Traditionally, formed sutures are passed through tissue with a needle and tied with a knot into a loop to close wounds and allow the healing of tissue. Minimally invasive surgery (MIS) and robotic surgery place demands on the surgeon's skill due to the need to tie suture knots in regions of the body which are inaccessible to the surgeon's hands. Many surgical instruments have been developed that assist the surgeon in knot tying or provide a knot substitute. Such instruments have been invented by the present inventor and others. One known instrument comprises a tool for the formation of welded loops of suture, and another considers the welded loop of suture itself as a surgical fastener. While this method of joining suture into stitches facilitates suturing in difficult to access regions of the body, in practice it requires an ultrasonic generator, transducer and wave guide to complete welds in monofilament suture. This apparatus is bulky and expensive, and requires straight-line access to the surgical site from the point of incision.

The present invention seeks to improve upon these earlier inventions through the use of a novel suture material and novel welding apparatus that does not require bulky, costly ultrasonic equipment and can be delivered through a slender and/or curved shaft.

Novel aspects of the disclosed invention include, among other things:

1. a suture material that is directly weldable using a small amount of simple low voltage electrical energy;

2. a tissue fastening device or construct comprising a continuous welded loop of filamentous material consisting of an electrically weldable polymer;

3. an apparatus for welding electrically weldable suture that offers precise control over weld parameters so as to ensure a consistent, high strength weld;

4. an apparatus for welding electrically weldable suture that can safely operate inside the body without damaging adjacent tissue; and 5. an apparatus for welding electrically weldable suture that can be delivered through a serpentine path to remote regions of a body.

These, and other, benefits can be achieved by the new material, apparatus, method and devices of the present invention.

The suture material aspect of the present invention is made of a filament of biocompatible material, of a diameter, strength and flexibility consistent with surgical suture, and electrically conductive with a predictable resistance value.

The apparatus aspect of the present invention includes a mechanism for holding the overlapping portion of a suture loop; a mechanism for applying contact pressure through the overlapping region; and a mechanism for applying and controlling electrical current through the overlapping region to cause localized heating of the overlapping region by the electrical current passing through the overlapping region and thereby causing localized melting of the overlapping region, which then re-solidifies so as to form a weld.

Some versions of the apparatus further include a mechanism for clamping the suture to maintain suture tension during the welding process; a mechanism for trimming suture tails extending past the suture loop; a handle with controls for allowing a user (e.g., a surgeon) to maneuver the apparatus and initiate the welding process; and an elongated straight, curved, articulating, flexible and/or steerable shaft connecting the distal welding apparatus to the proximal handle, allowing the user to maneuver the welding apparatus into regions of the body with difficult access (such as in MIS procedures).

Further versions of the apparatus include means for controllably or automatically penetrating tissue, passing suture, tensioning suture, trimming suture tails and releasing the formed tissue-fastening suture loop. Examples of these means are disclosed in prior U.S. Pat. No. 5,417,700 (which patent is hereby incorporated herein by reference) by the present inventor and may be used individually or in combination with this new welding apparatus.

The welding process aspect of the present invention shares many characteristics in common with resistance or spot welding of metals, with several important novel distinctions, including but not limited to: low voltage and special electrical isolation necessary for medical devices; the ability to work with non-metallic conductive materials; and means for controlling the localization and depth of material melt so as to preserve the high strength of the highly linearized molecular chains of the conductive polymer or the composite materials being welded.

The suture loop formed by the material, apparatus and process disclosed herein is a tissue-fastening device or construct in the form of a continuous loop formed in situ. The loop comprises a filament of the biocompatible, conductive material disclosed herein, arcing approximately in the configuration of a circle, with an overlapping region joined by a weld.

Also disclosed herein are other structures made of the disclosed material, and welded in situ, but not necessarily taking the form of a loop or comprising filamentous material of a uniform cross-section.

The Material Used to Form the Weldable Suture and/or the Weldable Structures

FIG. 1 shows a short length of filamentous biocompatible material 5. In one version of the present invention, material 5 has the characteristics of being substantially round in cross-section, and falling within the ranges dictated by United States Pharmacopeia for suture diameters (USP29-861) and tensile strengths (USP29-881) and equivalent international standards. Material 5 further has the characteristics of being electrically conductive with a known resistance, and meltable with a melting temperature above 37° C. (so that material 5 is in solid form in a human body). Thus, material 5 comprises an electrically conductive thermoplastic material.

In a preferred form of the invention, material 5 is a monofilament of a thermoplastic polymer compounded with a conductive additive. In some versions, a dispersant is used to assure uniform mixing of the conductive additive within the polymer matrix. In some versions, the base thermoplastic polymer and conductive additive (and dispersant, if required) are melt-compounded (mixed), extruded, and drawn to produce a monofilament with substantially linear molecular chains for superior strength and flexibility. In other versions, the melt-compounded (mixed) material is injection molded into single or multi-part devices for medical applications. In some versions, the thermoplastic polymer is a bio-absorbable material currently approved for use as a suture or implant material (e.g., Polylactic Acid (PLA), Polyglycolide (PGA), Polydioxanone (PDS), a thermoplastic linear polyester such as that sold under the tradename TephaFLEX™, etc.). In other versions, the thermoplastic polymer is a non-absorbable material (e.g., Nylon, Polypropylene, Polycarbonate, etc.). In some versions, the conductive additive is an inert and/or non-toxic material such as carbon black, carbon fiber, iron oxide ($Fe_2O_3$ and others) or metallic powders or nanoparticles. In other versions, the conductive additive is any one of intrinsically conducting polymers (ICPs) including, but not limited to, polyacetylene, polyaniline, polythiophene, polyphenylenevinylene. In some versions, these non-thermoplastic polymers are compounded with thermoplastic base polymers. In other versions, the non-thermoplastic polymers are applied as a film coating to a base polymer filament or part. In some versions the conductive coating is a continuous or patterned coating of conductive ink. In some versions a conductive polymer or composite may be co-extruded on the outside of another not necessarily conductive polymer at its core. In a version the core material has a higher melting temperature than the co-extruded outside layer. In other versions, the filament may be a multi-strand structure such as braided suture made of bundles of microfilaments of conductive thermoplastic polymer, or a composite of different filaments braided together. In one version, conductive and non-conductive filaments are combined into a single braided suture. In another embodiment, microfilaments of varying melt temperatures and conductivity are braided together such that localized weld melting does not melt filaments of higher melting temperature, thereby preserving their highly linearized molecular orientation and high strength characteristics and producing a strong weld region. In one version, high strength, high-melt-temperature polymer filaments are provided in a low-melt temperature metallic matrix such that when applying electric current through adjacent portions of the polymer filament/metal matrix, the metal fuses but leaves the high strength filaments undamaged. In still another version, metallic suture or wire is used, however, pure metal is generally less desirable than conductive thermoplastic because high melt temperatures of metals and high thermal conductivity in metals risk damage to surrounding tissue, and melt spread in metals is more difficult to control than melt spread in polymers. In a version of the material, the material filament has transverse (side-to-side) conductivity but not axial (end-to-end) conductivity, which has the benefit of protecting the body from stray electrical current in the event of a break in the suture before or during welding. The transverse but not axial conductivity feature may result from drawing or stretching a composite material with a low conductive additive fill ratio, since the chain of additive may be broken axially during stretching but compacted transversely due to diameter reduction.

In one form of the invention, material 5 is a conductive thermoplastic polymer.

Apparatus for Welding Conductive Thermoplastic Suture

Figure 2:
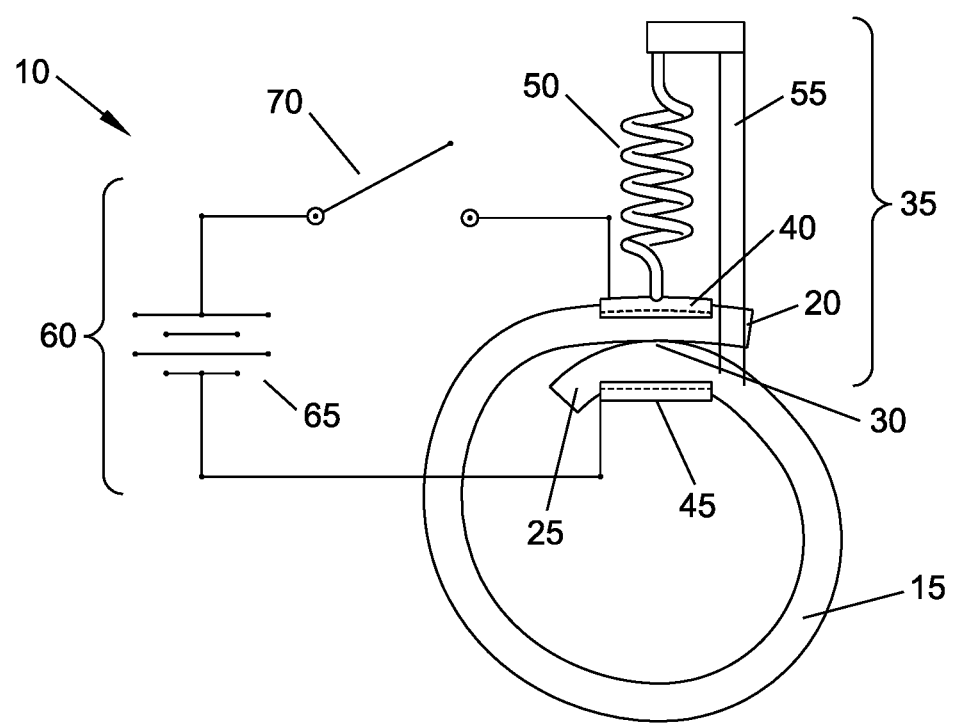
FIG. 2 is a schematic view showing novel apparatus for welding conductive thermoplastic suture.
Figure 2A:
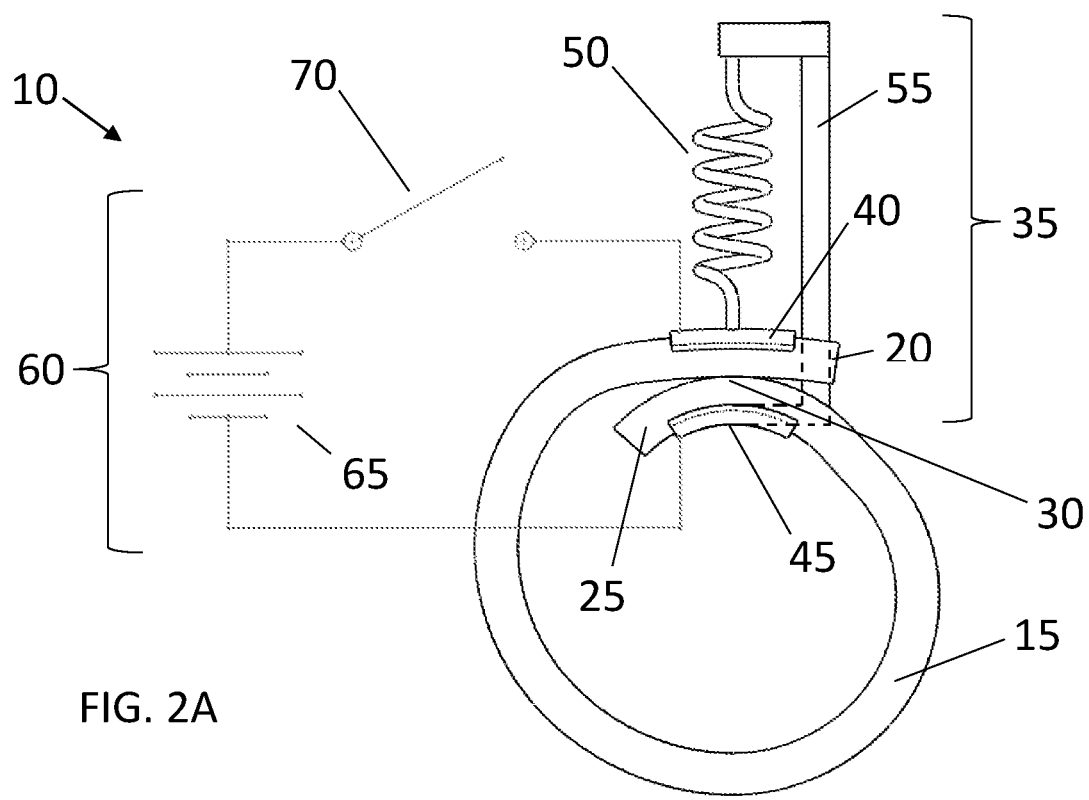
FIG. 2A is a schematic view showing novel apparatus for welding conductive thermoplastic suture.

FIG. 2A shows an apparatus 10 for welding a length of conductive thermoplastic suture 15. The length of conductive thermoplastic suture 15 comprises a first end 20 and a second end 25. First end 20 and second end 25 overlap at a contact point 30 so as to form a loop of suture 15. The loop of suture is held in its loop configuration by a clamping mechanism 35 applied at contact point 30. Clamping mechanism 35 comprises a first electrode 40 conforming to the surface of first end 20 of suture 15 and a second electrode 45 conforming to the surface of second end 25 of suture 15. A spring 50 applies a predetermined force between electrodes 40, 45 so as to maintain pressure on contact point 30. In one version, first electrode 40 and second electrode 45 are disposed substantially parallel to one another, resulting in line contact between first suture end 20 and second suture end 25 (FIG. 2). In another version (i.e., the version shown in FIG. 2A), there is a relative curvature between first electrode and second electrode 45, resulting in a point contact between first suture end and second suture end 25. A structural frame 55 holds the components of the clamping mechanism (i.e., first electrode 40, second electrode 45 and spring 50) in place. Importantly, structural frame 55 is non-conductive between first electrode 40 and second electrode 45. An electrical circuit 60 comprising, at a minimum, a power source 65 and a switch 70, is connected to first electrode 40 and second electrode 45 as shown in FIG. 2A such that closing switch 70 applies a voltage across first electrode 40 and second electrode 45 and allows current to flow through first suture end 20 and second suture end 25 at contact point 30. Preferably, power source 60 comprises a DC battery, but in other versions, power source 60 may comprise an exterior AC power source with an isolation transformer and a rectifier, or a low- or high-frequency AC power source.

In other versions of the present invention, additional features may be added to apparatus 10 in order to facilitate its use as a surgical instrument, such as tissue penetrating and suture passing means; tensioning means; clamping means to secure suture ends 20, 25 so as to facilitate welding with the suture under tension; suture tail trimming means; weld region drying gas introduction means; an elongated and/or serpentine delivery shaft; and/or a handle for manual user interface or an electro-mechanical interface for connection to a surgical robot. These additional means and features are well known in the art and described in detail in prior patents (e.g., U.S. Pat. No. 5,417,700) by the present inventor and others.

Figure 2B:
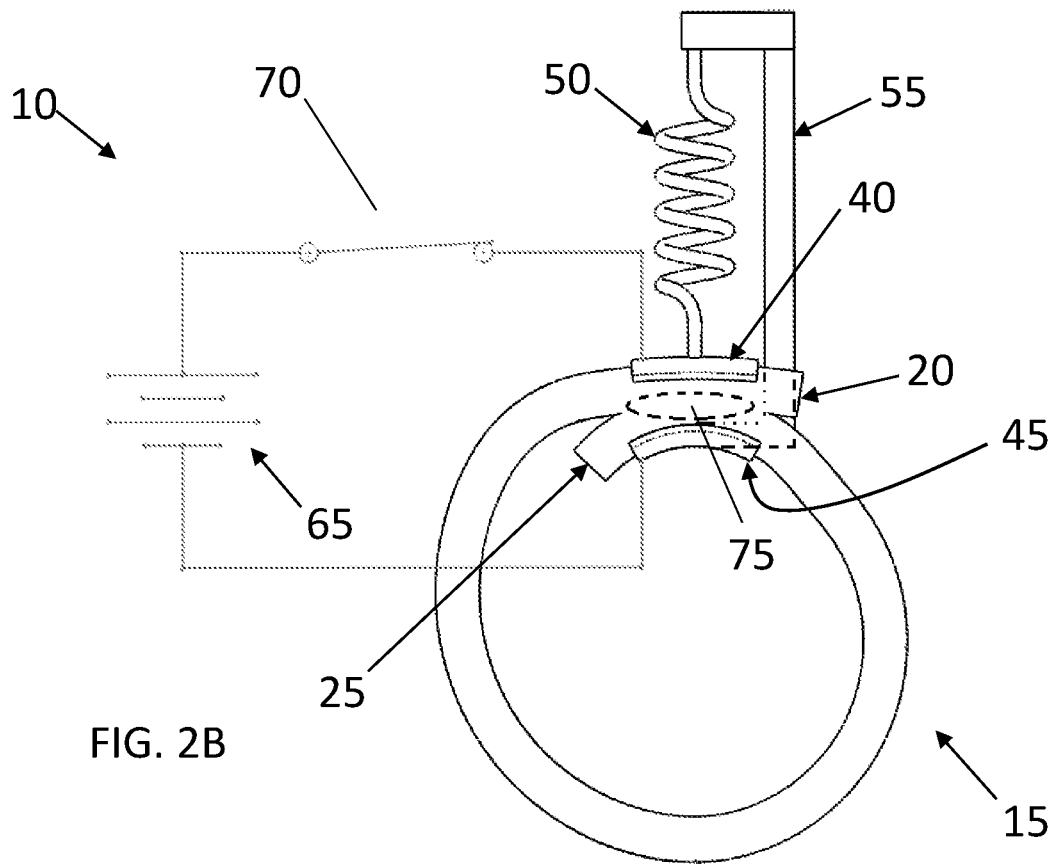
FIG. 2B is a schematic view showing the formation of a weld in conductive thermoplastic suture using the novel apparatus of FIG. 2A.

An illustrative method and process for forming a weld in conductive thermoplastic suture 15 is shown in FIG. 2B. Closing switch 70 causes current to flow from first electrode 40, through first suture end 20, across contact point 30, through second suture end 25 and then to second electrode 45. The highest resistance in this circuit is at contact point 30, resulting in heat build-up taking place in this region and spreading into first suture end 20 and second suture end 25. The heat build-up results in a localized melt region 75 that spreads into first suture end 20 and second suture end 25 as the heat increases. In one version, switch 70 is opened and the current stopped before the melt spreads across the full cross-section of the suture material. This differs from conventional resistance welding of metal where the full metal thickness is usually desired to be involved in the weld and is due to the non-isotropic nature of drawn, extruded monofilament suture.

In order to repeatedly and reliably achieve the optimum depth of melt penetration into suture ends 20, 25, a number of process control methods may be employed. In many of these process control methods, we will be referring to circuitry and components not shown in the simplified schematic shown in FIGS. 2A and 2B, such as a microprocessor and various sensors, however, they can be assumed to be deployed in the conventional manner familiar to those skilled in the art. In one such version, a simple timer is used to control the amount of time that the weld circuit is switched on. In another version, first and second electrodes 40, are configured such that as melting spreads, electrodes 40, 45 move toward each other as the melted material is displaced, and electrodes 40, 45 contact each other when the optimum amount of material has melted. The contacting electrodes short together, shunting current around the suture and stopping the heating. A current sensor may then be used to signal a microprocessor to interrupt the weld circuit. In another version, a displacement sensor may be substituted for the self-contacting electrodes to signal a microprocessor to shut off the circuit when the desired weld displacement has occurred. Other versions employ temperature sensors to control the weld circuit through a microprocessor, shutting off the weld circuit when a pre-set peak temperature or thermal distribution has been sensed. In still other versions, combinations of time, displacement and temperature sensors are employed and optimum weld parameters are determined by a microprocessor-based algorithm.

Tissue Fastening Device Or Construct Formed By Welded Suture

Figure 3:
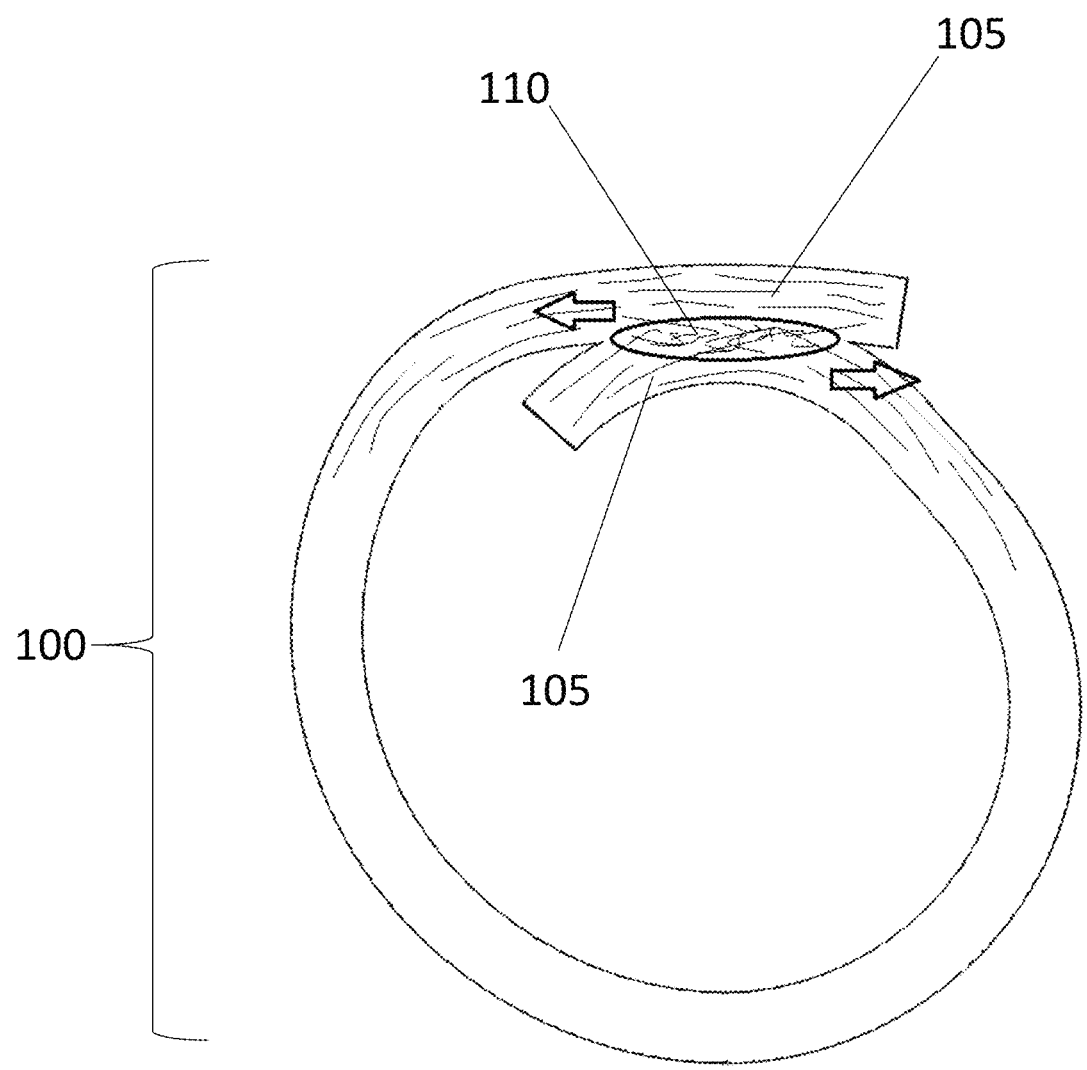
FIG. 3 is a schematic view showing a tissue fastening device or construct formed in accordance with the present invention.

FIG. 3 shows a tissue fastening device or construct 100 having a length of electrically conductive thermoplastic material formed into a continuous loop in situ, and joined by a partial depth penetration weld. In this figure, we see regions of virgin monofilament 105 with high tensile strength resulting from highly linearized molecular chains, notionally represented by lines roughly parallel to the suture axis, surrounding a weld region 110 with amorphous molecular orientation, notionally represented by random, disorganized lines. The tensile strength of the virgin monofilament is significantly stronger than that of the re-melt region. When tension is placed on the loop, the top and bottom portions of the overlapping loop ends load the weld region in shear, and since the area of the weld region is greater than the cross-section of the suture, the stress in this region is reduced as long as there is virgin high strength suture material on both sides of the weld region to distribute the load.

Tissue-Securing Devices of Molded Thermoplastic Material

Figure 4A:
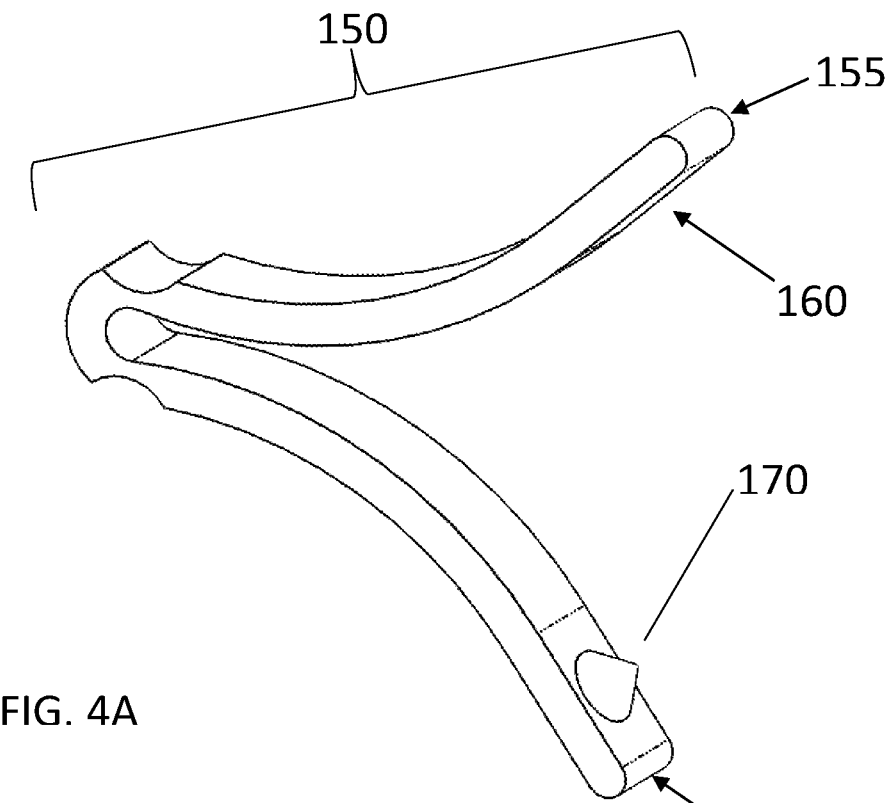
FIGS. 4A and 4B are schematic views showing a novel device made of molded conductive thermoplastic material that is intended to be electrically welded in situ.
Figure 4B:
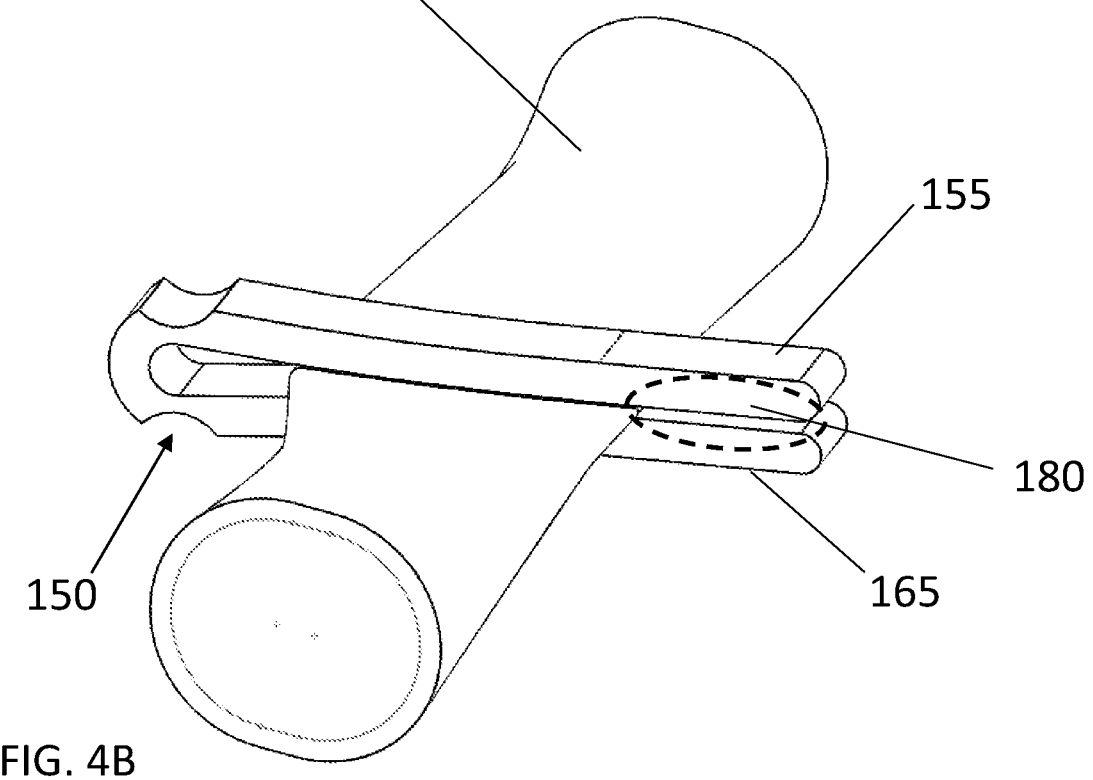

FIGS. 4A and 4B show a clip 150 made of molded conductive thermoplastic material that may be electrically welded in situ, e.g., to occlude vessels such as veins and arteries for surgical hemostasis, or to clamp together tissue, etc. FIG. 4A shows clip 150 prior to deployment. Clip 150 comprises a first end 155 having a recess 160 and a second, opposing end 165 having a protruding feature 170. Protruding feature 170 on second end 165 mates with recess 160 on first end 155 so as to create a contact point of high resistance to initiate the weld melt. FIG. 4B shows clip 150 welded in situ around a blood vessel 175. Electrodes (not shown) applied to facing surfaces of first end 155 and second end 165 on clip 150 initiate a weld melt region 180 and bond first end 155 and second end 165 to one another so that clip 150 occludes blood vessel 175.

Figure 5A:
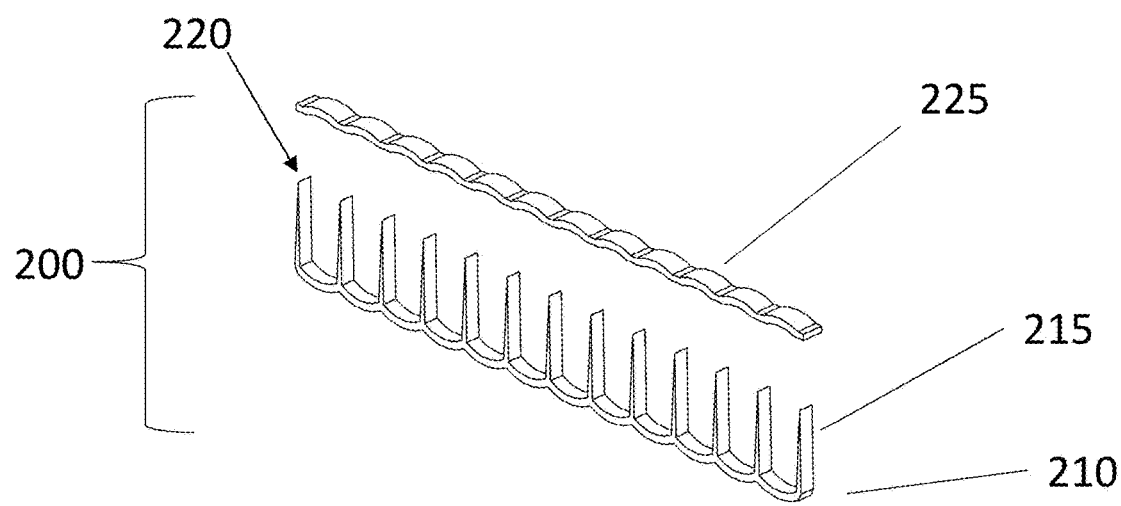
FIGS. 5A and 5B are schematic views showing another novel device made of molded conductive thermoplastic material that is intended to be electrically welded in situ.
Figure 5B:
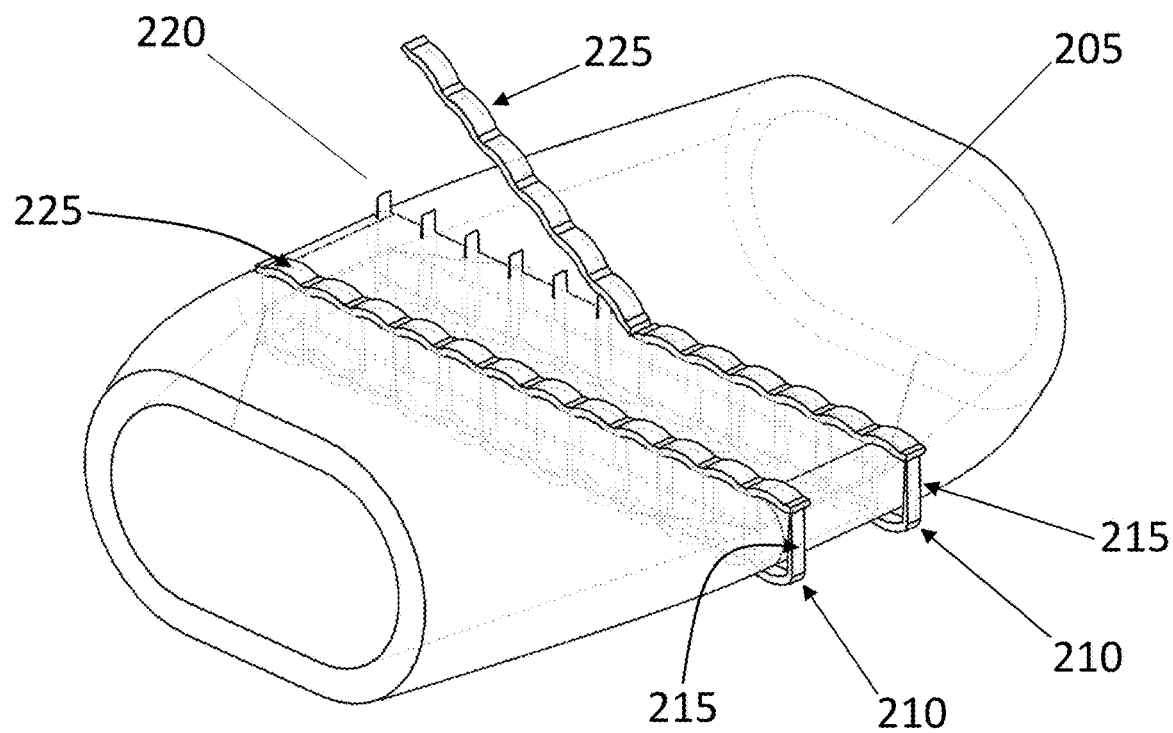

FIGS. 5A and 5B show another illustrative device 200 made of molded conductive thermoplastic material that is electrically welded in situ to occlude a section of a hollow organ 205, such as a stomach, to allow the organ to be surgically divided. Device 200 comprises (i) a first strip 210 having a row of conductive thermoplastic needles 215 terminating in needle tips 220, and (ii) a second strip 225 having counterpart recesses (not shown) for receiving needle tips 220. In this version of the invention, an apparatus (not shown) delivers first strip 210 of conductive thermoplastic needles 215 through two layers of the organ (i.e., through the two side walls of the hollow organ) and second strip 225 is welded to the needle tips 220 of first strip 210 after needle tips 220 have penetrated and emerged from the organ. By controlling the depth of melting of needles 215, the distance between the top portion (i.e., second strip 225) and bottom portion (i.e., first strip 210) of device 200 can be controlled, thereby controlling the degree of "squeeze" applied to the organ and accommodating organs with variable thickness. In this way, welded surgical fasteners functionally similar to a row of stitches or surgical staples may be delivered in a continuous linear process.

Suturing Instrument

Figure 6:
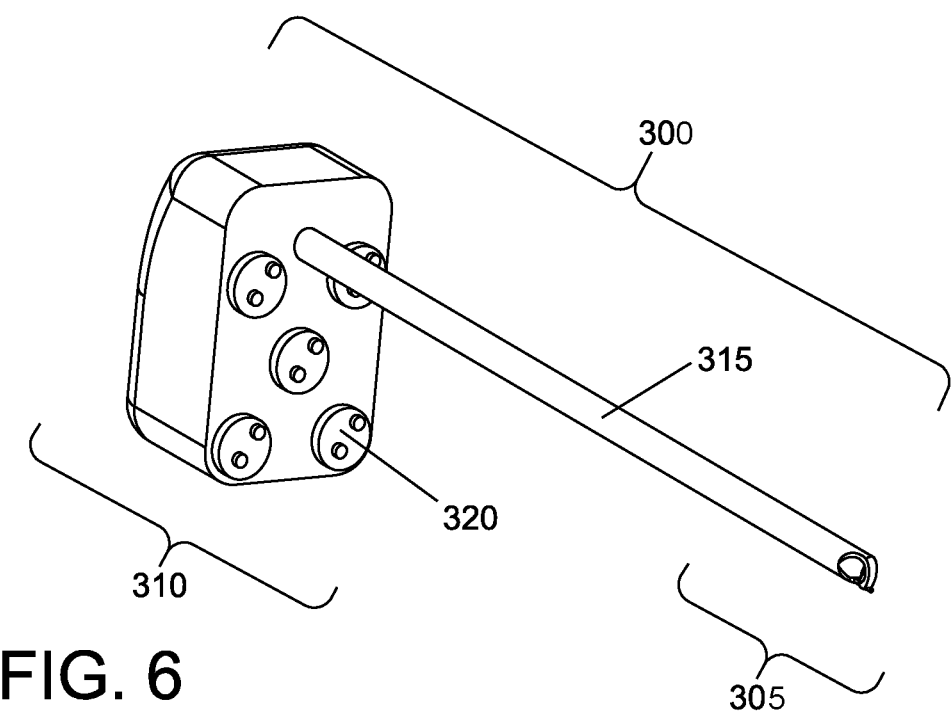
FIG. 6 is a schematic view showing a novel suturing instrument for use in surgery.

FIG. 6 shows a suturing instrument 300 for surgery comprising a distal end 305 and a proximal end 310 connected by a shaft 315. Distal end 305 is an end effector and includes mechanical and electrical means for manipulating tissue and suture material for the formation of surgical stitches. Proximal end 310 contains actuating means for driving and operating the stitch-forming means at distal end 305 through wires and linkages (not shown in FIG. 6) passing through shaft 315. Shaft 315 has sufficient length to reach anatomical structures within the interior of a body, with proximal end 310 of the instrument remaining outside of a body, distal end 305 reaching target tissue at a surgical site, and shaft 315 passing through intervening tissue and spaces, e.g., by passing through a small incision in a body wall such as the abdominal wall. In one version (not shown), proximal end 310 of instrument 300 includes a handle adapted to be held by a human hand and the actuating means on proximal end 310 includes various buttons, triggers, levers, etc. for controlling the stitch-forming means at distal end 305, and a battery for supplying power to weld the suture. In another version (also not shown), the handle contains motors, linear actuators, pneumatic or hydraulic cylinders, or other actuation means to drive the stitch-formation means, a microprocessor-controlled circuit to sequence the stitch formation and welding, a trigger or button to initiate the stitch formation process, and a battery to power the actuators and circuit. Still other versions have a handle and external power means such as a power cord or pneumatic or hydraulic hoses. In another version (shown), proximal end 310 includes electrical and/or mechanical interfaces 320 for connection to a surgical robot.

Figure 7A:
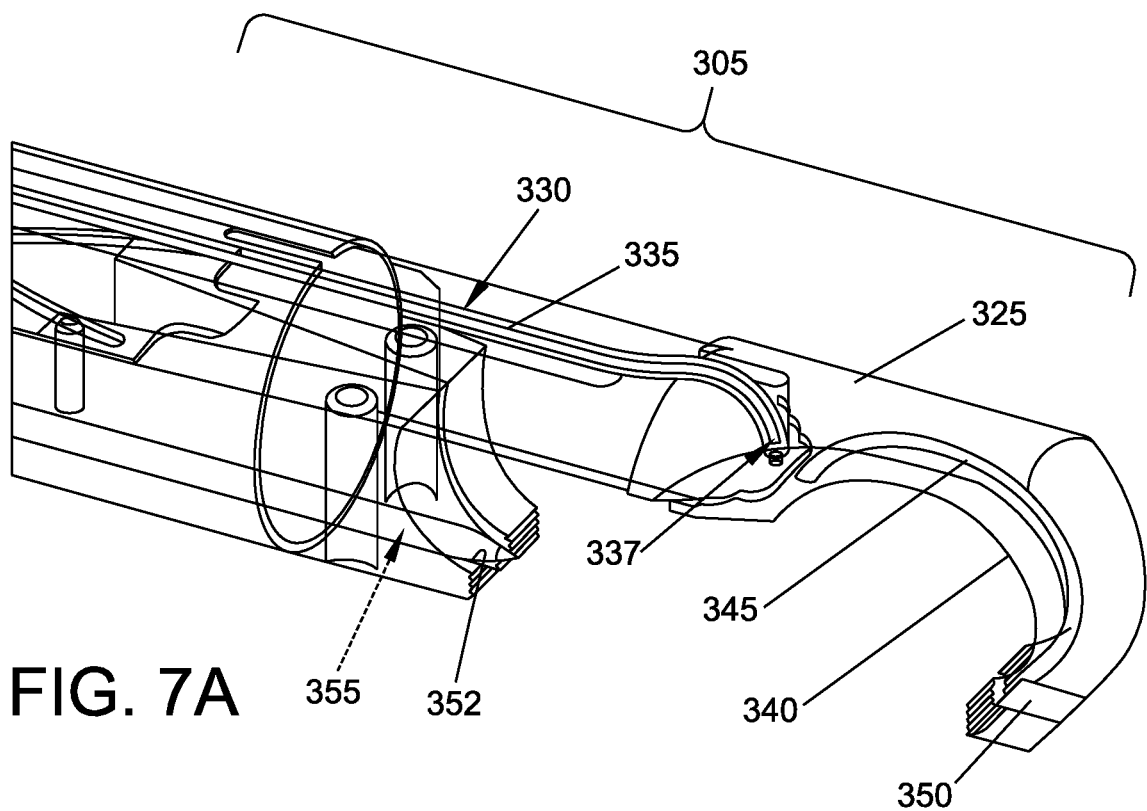
FIG. 7A is a schematic view showing the distal end effector portion of the novel suturing instrument of FIG. 6.

FIG. 7A shows a version of a distal end effector 305 for surgical stitching instrument 300 (or other surgical stitching instrument). Distal end effector 305 comprises a slidable grasper 325 for grasping a piece of tissue and means for passing and welding a loop of suture about the grasped tissue, as will be discussed in further detail below.

Slidable grasper 325 includes a passage 330 for passing a length of conductive thermoplastic polymer monofilament suture 335 (having a distal end 337) therethrough, a hook feature 340 with a groove 345 opening on the inside of hook feature 340, and a needle hole 350 aligning with groove 345 of hook feature 340. Slidable grasper 325 also comprises a bore 352 for passing a needle 355 therethrough.

Figure 7B:
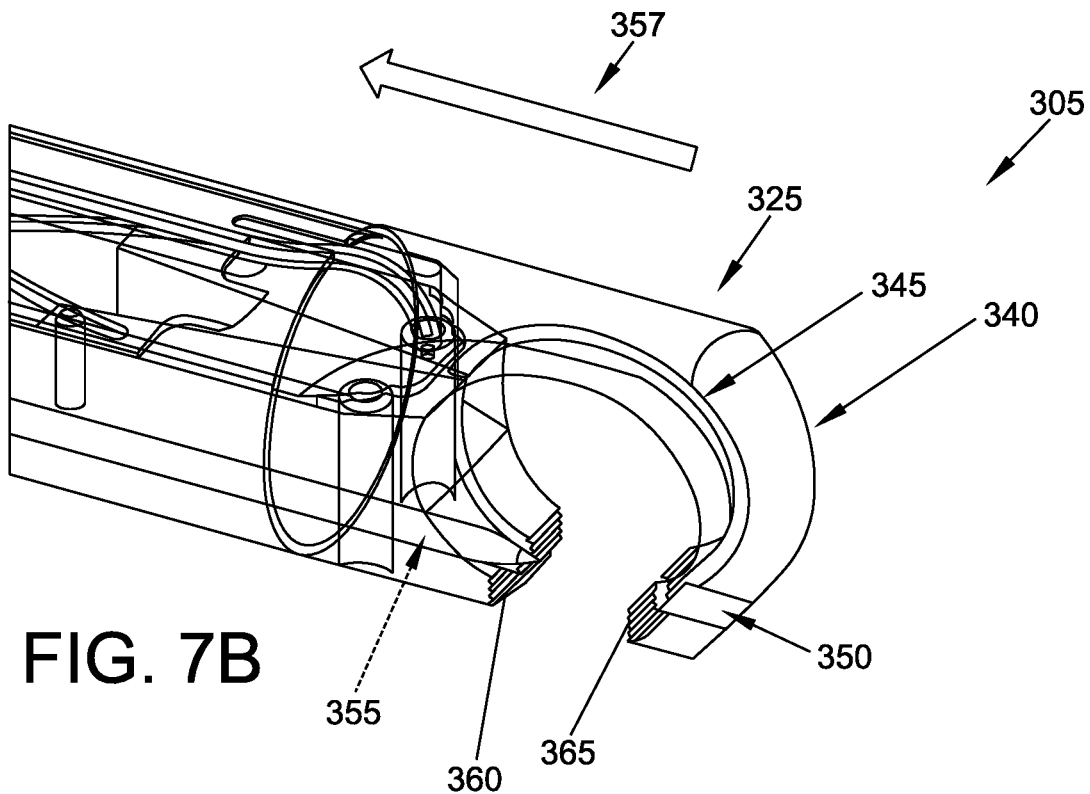
FIG. 7B is a schematic view showing actuation of the grasper portion of the distal end effector shown in FIG. 7A.

In use, and looking now at FIG. 7B, hook feature 340 of slidable grasper 325 is moved proximally (i.e., in the direction of arrow 357) so as to pinch the tissue to be sutured (not shown) between a first textured grasping surface 360 and a second textured grasping surface 365.

Figure 7C:
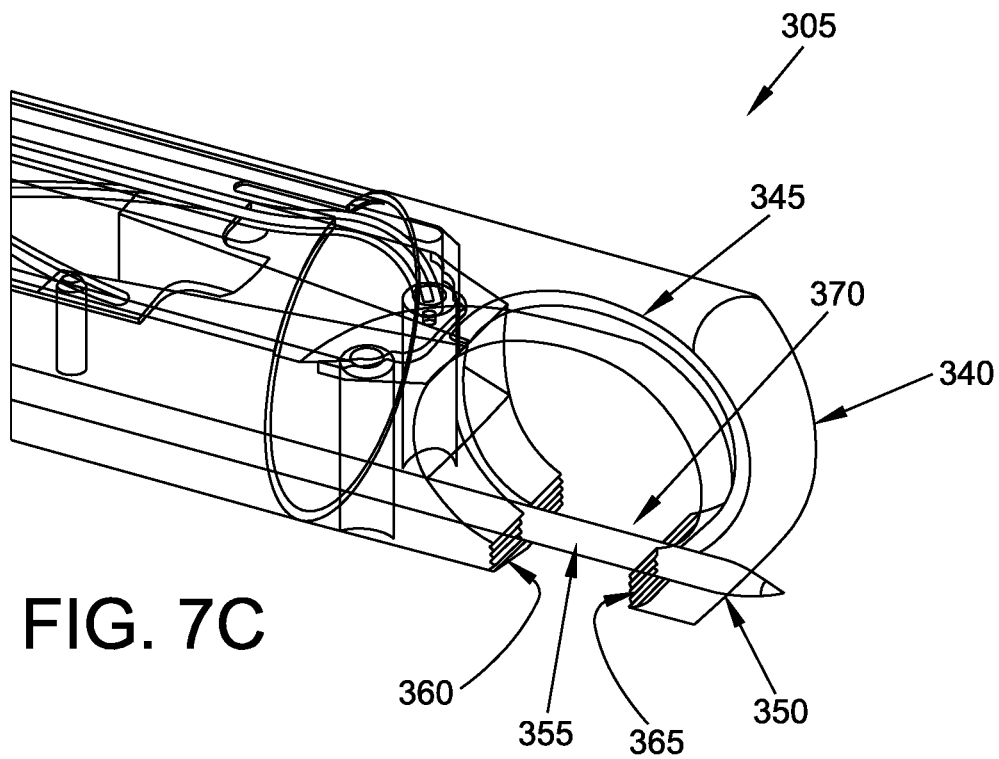
FIG. 7C is a schematic view showing a needle (having a groove) advanced through the tissue (not shown) pinched between the grasping surfaces of the distal end effector.

Looking now at FIG. 7C, needle 355 comprises a groove 370 so that after needle 355 has been advanced through the tissue (not shown) which is pinched between grasping surfaces 360, 365 and needle 355 is disposed in needle hole 350 of hook feature 340, groove 370 in needle 355 is aligned with groove 345 in hook feature 340, whereby to form a continuous circular path (i.e., by means of groove 345 of hook feature 340 and groove 370 in needle 355).

Figure 7D:
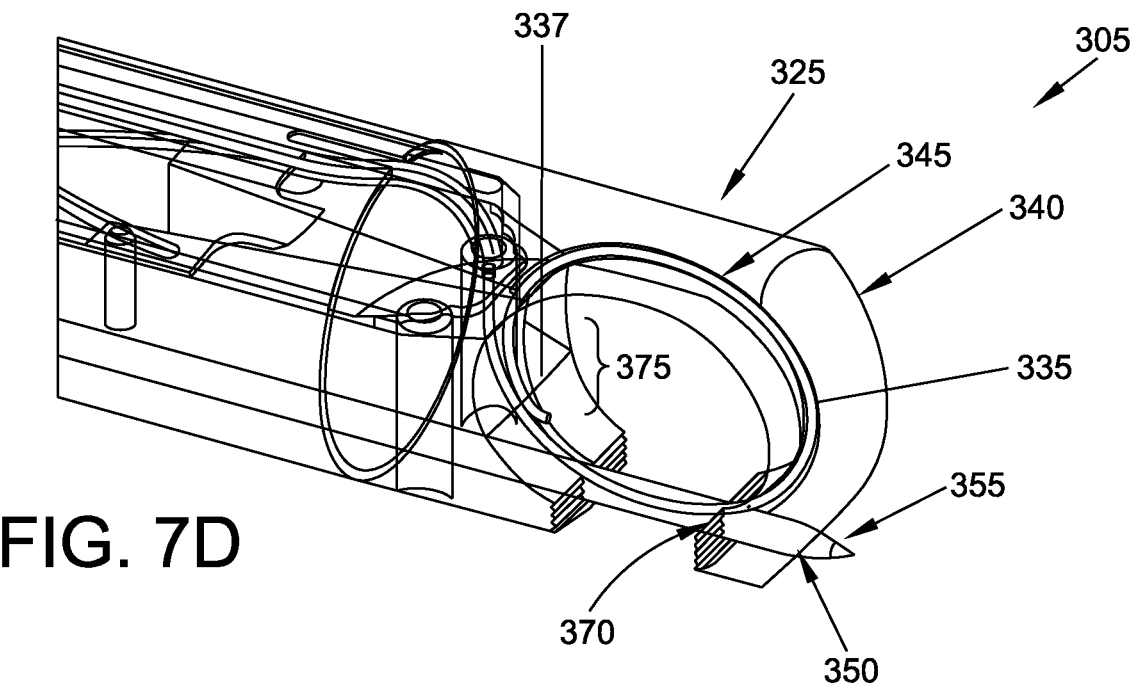
FIG. 7D is a schematic view showing the distal end effector of FIG. 7C, with a suture advanced by pushing the suture into the groove of the needle and a groove of the grasper.

Looking next at FIG. 7D, suture 335 may be advanced through the continuous circular path formed by groove 370 of needle 355 and groove 345 of hook feature 340 until distal end 337 of suture 335 passes back over a portion of suture 335 proximal to distal end 337, whereby to form a loop of suture passing through the tissue captured in distal end effector 305, with distal end 337 of suture 335 contacting the proximal portion of suture 335 at overlapping region 375. Suture 335 is advanced by motor-driven rollers in shaft 315 and/or proximal end 310 of instrument 300 which engage and push suture 335 through the circular path, or by other driving means in shaft 315 and/or proximal end 310 of instrument 300 (not shown) known to those skilled in the art.

Figure 7E:
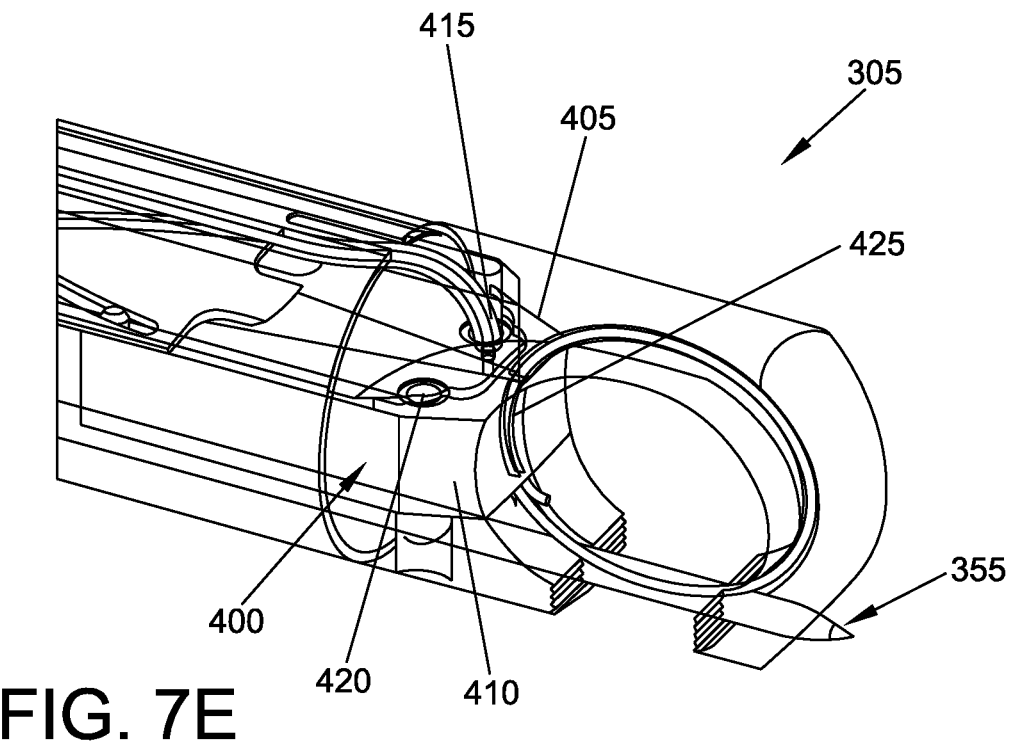
FIG. 7E is a schematic view showing actuation of the articulating gripping mechanism of the distal end effector of FIG. 7D.

After suture 335 has been advanced through the aforementioned circular path so as to form the loop of suture, an articulating gripping mechanism 400 may be used to firmly grasp distal end 337 of suture 335 adjacent the proximal portion of suture 335 at overlapping region 375, leaving proximal portion of suture 335 free to slide axially for tensioning. To this end, and looking now at FIG. 7E, articulating gripping mechanism 400 comprises a first lever 405 and a second lever 410 which pivot about pins 415 and 420, respectively. When suture 335 is being advanced through groove 370 of needle 355 and groove 345 of hook feature 340, levers 405, 410 are held apart, creating a gap in line with groove 370 in needle 355 and circular groove 345 of hook feature 340, thereby allowing distal end 337 of suture 335 to pass through the gap in order to form the loop of suture. After distal end 337 of suture 335 is in place at overlapping region 375, levers 405, 410 are closed on distal end 337 of suture 335, grasping distal end 337 and holding it firmly in place in overlapping region 375. Levers 405, 410 are made of a non-electrically-conductive material except for a first electrode 425 disposed where levers 405, 410 grip distal end 337 of suture 335. Electrode 425 only makes electrical contact with distal end 337 of suture 335.

Figure 7F:
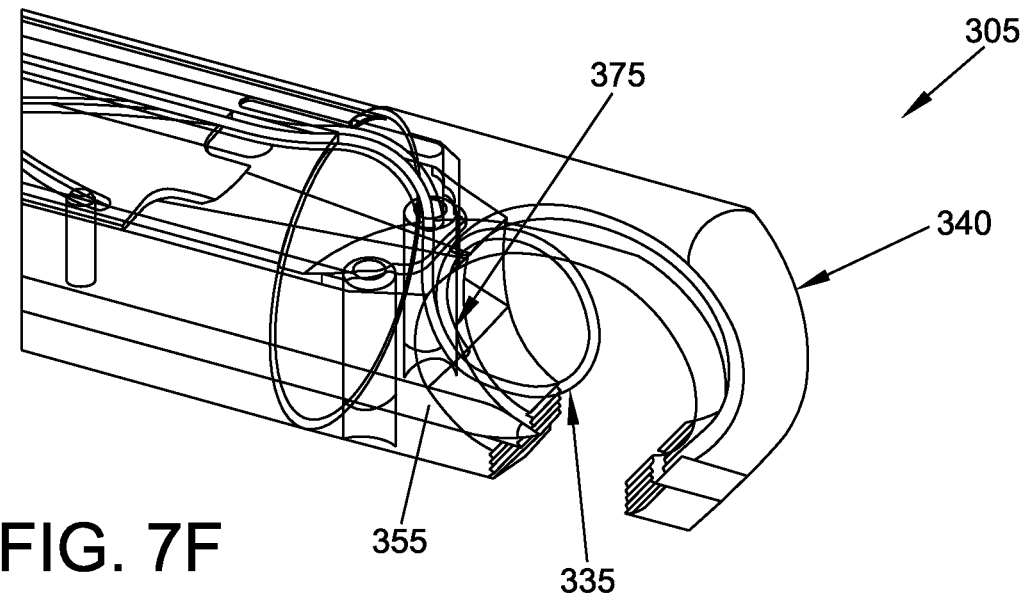
FIG. 7F is a schematic view showing the distal end effector of FIG. 7E, with the needle retracted and a suture advancement mechanism reversed.

After distal end 337 of suture 335 is clamped by levers 405, 410 in overlapping region 375, needle 355 is retracted and the suture advancement means that advanced suture 335 through the circular path is reversed so as to retract the loop of suture 335 and tighten the loop of suture 335 around the tissue grasped by slidable grasper 325 (FIG. 7F).

Figure 7G:
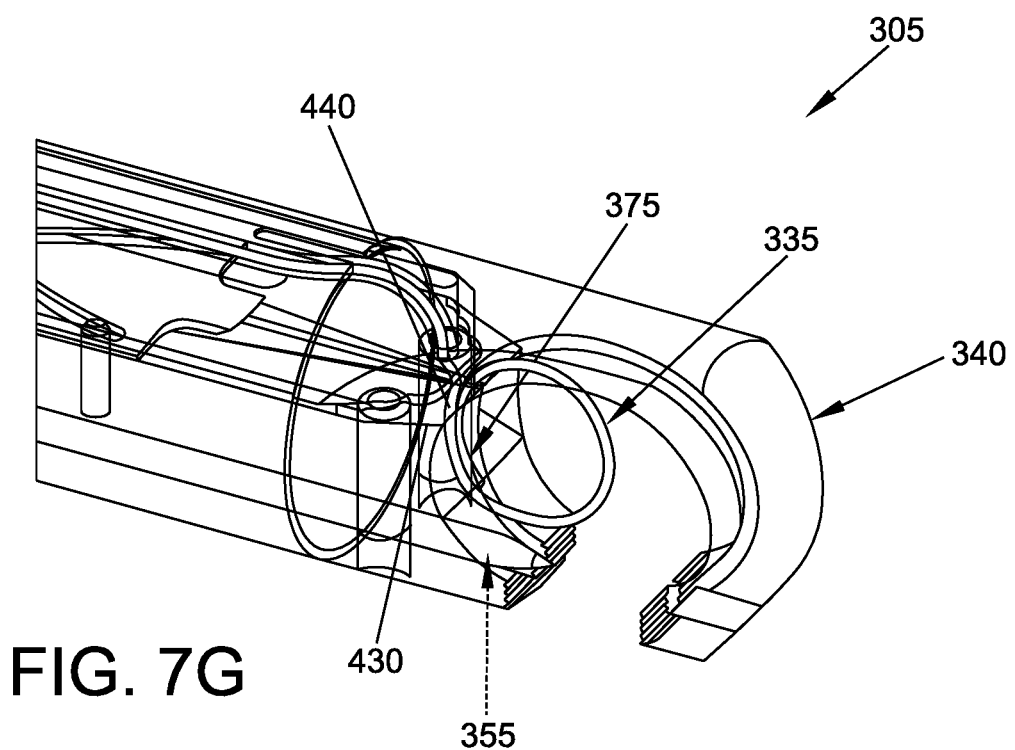
FIG. 7G is a schematic view showing the distal end effector of FIG. 7F, with an electrode advanced to contact a portion of the suture.

Once the loop of suture has been tightened around the tissue (not shown), a second electrode 430 is advanced to contact the portion of suture that overlaps with distal end 337 of suture 335 (i.e., portion 440 of FIG. 7G) in overlapping region 375. Voltage potential is applied across first electrode 425 and second electrode 430 and current flows across the overlapping suture region 375, thereby causing heating, melting and the formation of a weld in accordance with the method described above in relation to FIG. 2A.

Figure 7H:
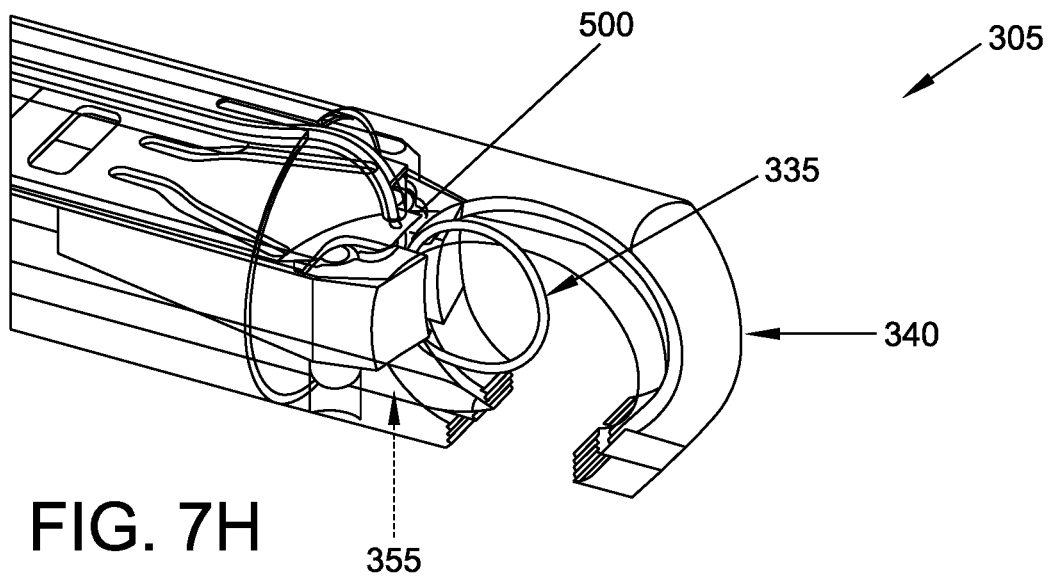
FIG. 7H is a schematic view showing the distal end effector of FIG. 7G, with a knife blade advanced to cut the suture.
Figure 7I:
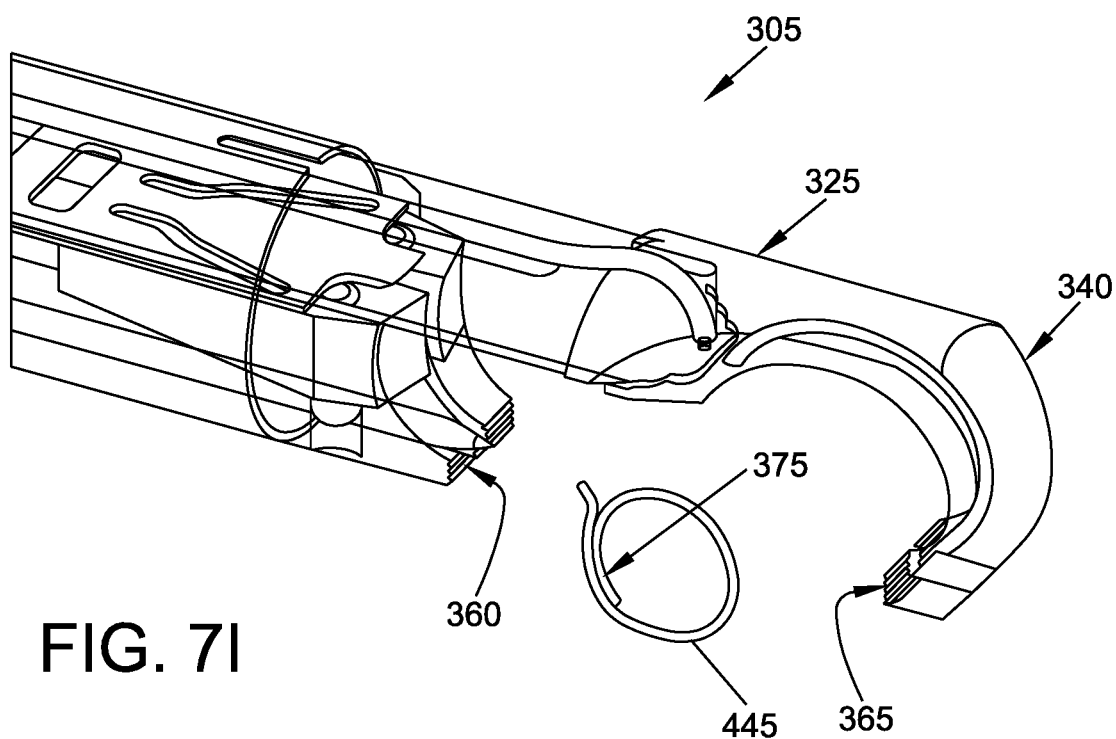
FIG. 7I is a schematic view showing the distal end effector of FIG. 7H, with the grasper in a re-opened position.

After welding distal end 337 of suture 335 to the proximal portion of the suture at overlapping suture region 375, a knife blade 500 is advanced to cut the suture supply proximal to the weld so as to separate the welded loop from instrument 300 (FIG. 7H). Hook feature 340 of slidable grasper 325 is then moved distally so as to re-open slidable grasper 325, thereby releasing the pinched tissue. First lever 405 and second lever 410 are also separated to release the welded loop stitch 445 surrounding the tissue (FIG. 7I). The actuators at proximal end 310 of instrument 300 then return distal end effector 305 to the position of FIG. 7A and instrument 300 is ready to form another stitch.

It should be understood that a wide range of additional devices and systems can use the disclosed material, apparatus and method and are included in the scope of the present disclosure.

End Effector for Use in Robotic Surgery

Figure 8A:
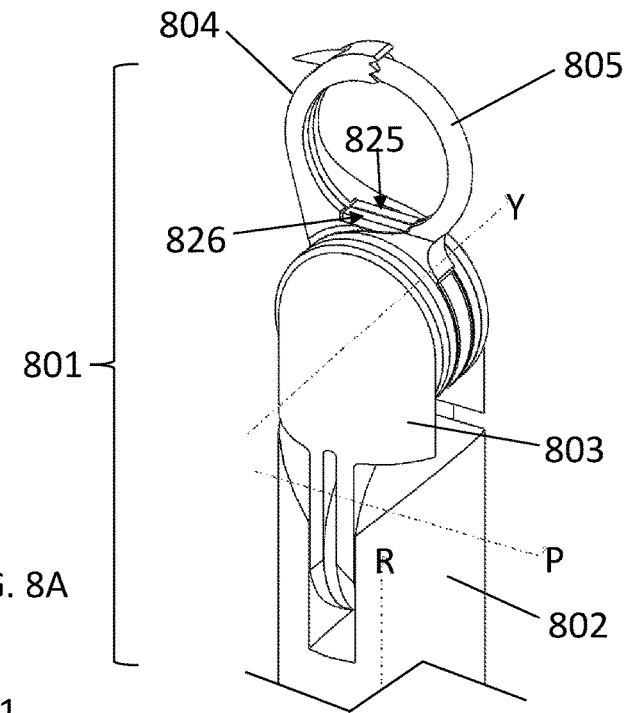
FIGS. 8A and 8B are schematic views showing a novel end effector for use in robotic surgery.

FIG. 8A shows a version of the present invention incorporated into a highly articulated end effector 801 for robotic surgery. This embodiment includes a four degree of freedom (DoF) slave-robot end effector controlled remotely by a surgeon stationed at a master-robot control console. The principal degrees of freedom include: an instrument shaft 802 rolling about axis R, a mid-section "knuckle" 803 articulating in pitch about axis P, and first (804) and second (805) independently rotating tool elements disposed in opposition to each other, each rotating about yaw axis Y. Other robotic end effectors employ articulating segments or other means to achieve four or five DoF motion, and the present invention applies to these devices also. The end effector described thus far in this paragraph is known to the art and is in common usage in robotic surgery. We will now describe novel aspects unique to the present invention.

Figure 8B:
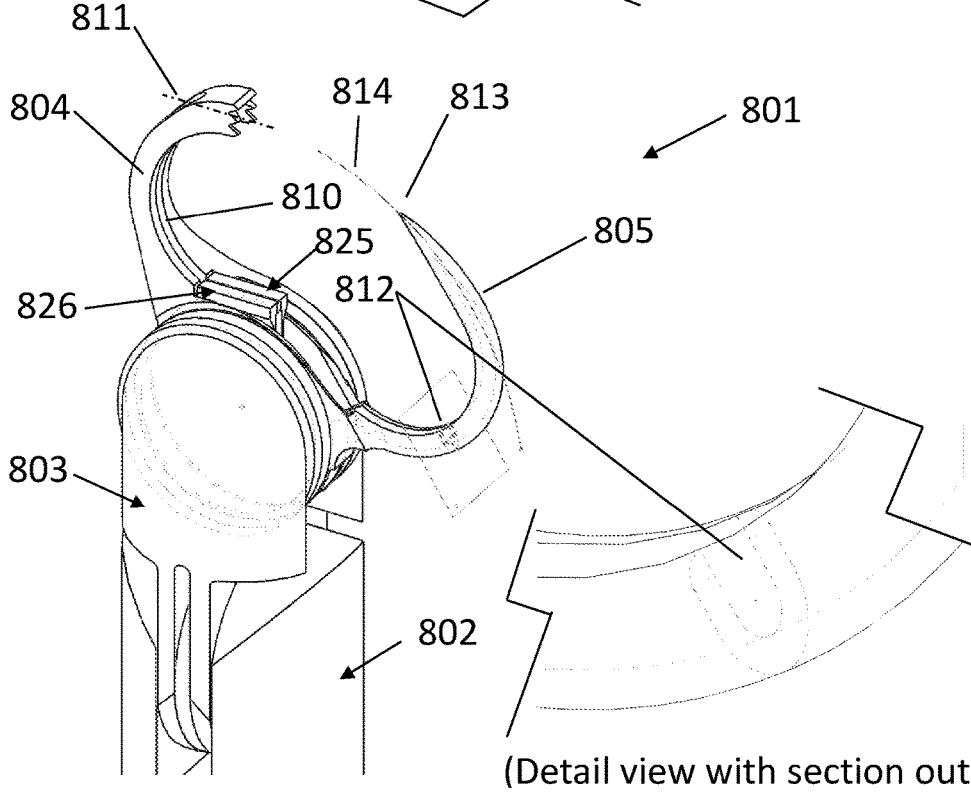

FIG. 8B shows an embodiment of the present invention that forms a suture stitch in the same manner as the invention described in FIGS. 7A through 7I, but differs through the addition of a highly articulated end effector (e.g., the end effector of FIG. 8A). In an embodiment, first articulating opposed tool element 804 is a semi-circular shaped rigid body with an inward facing groove 810 terminating in a needle hole 811 at its distal end. Second tool element 805 is a semi-circular shaped needle with an inward facing suture groove 812 and a sharp tissue penetrating point 813 on its distal end. The distal portion of the needle 805 (i.e., second tool element 805) has a radius 814 to align with needle-receiving hole 811 in tool element 804. When first and second tool elements 804 and 805 are closed in opposition (as shown in FIG. 8A), inward facing grooves 810 and 812 form a continuous groove through which suture may be advanced.

Figure 8C:
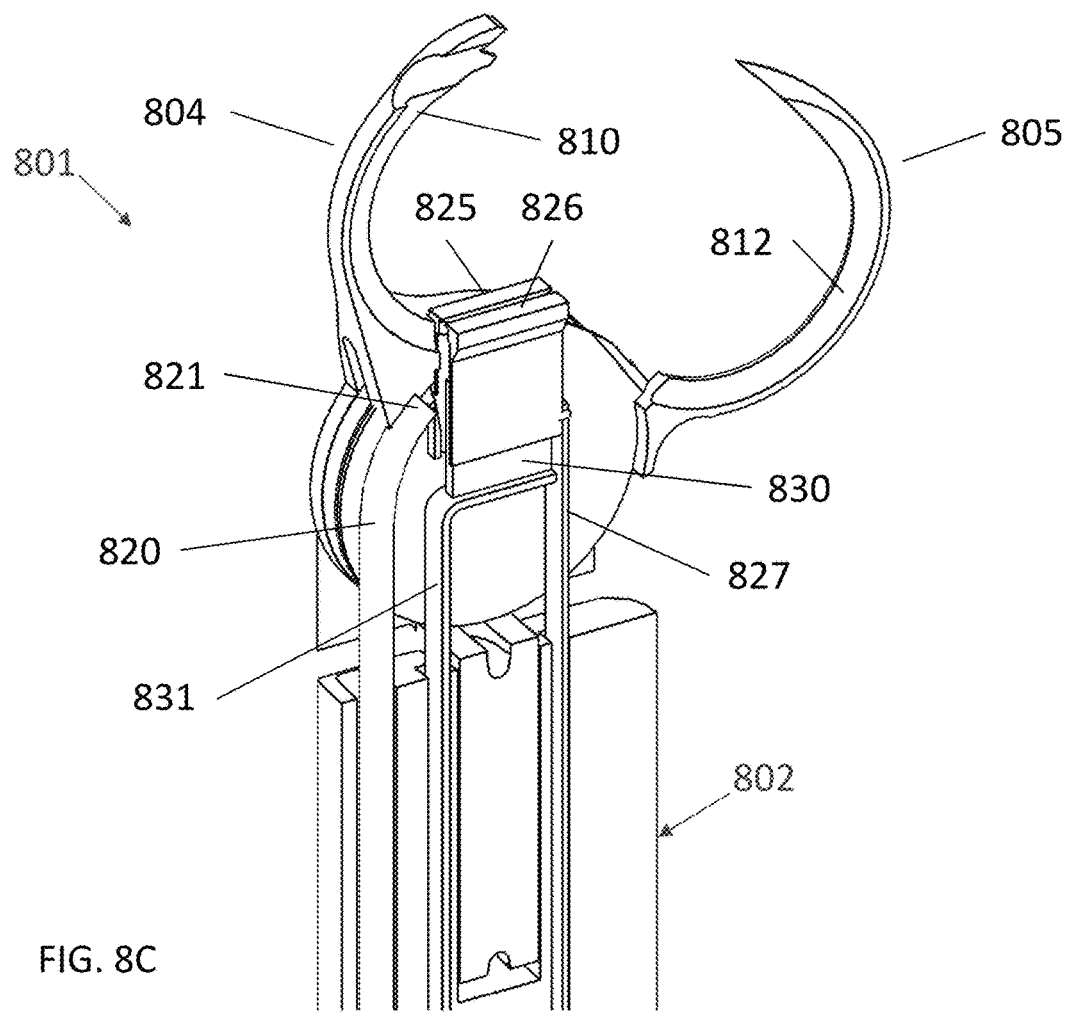
FIGS. 8C-8F are schematic views showing further details of the novel end effector shown in FIGS. 8A and 8B.

FIG. 8C shows a partial section view of an embodiment of the present invention schematically displaying the means for forming a suture stitch with the end effector. A flexible suture delivery tube 820 aligns with grooves 810 and 812 in opposing tool elements 804 and 805 when tool elements 804 and 805 are closed in opposition. The distal end 821 of the suture delivery tube 820 is fixed relative to first tool element 804 (in other embodiments the mechanism may be reversed and delivery tube 820 may be fixed to second tool element 805). The flexibility of the suture delivery tube 820 allows the suture delivery tube to maintain its alignment with first tool element 804 throughout the full range of motion of the articulating end effector. The flexible suture delivery tube 820 serves the same purpose as the suture passage 202 described in FIG. 7A, with the difference of being flexible and allowing articulation of the end effector.

Figures 8D, 8E, 8F:
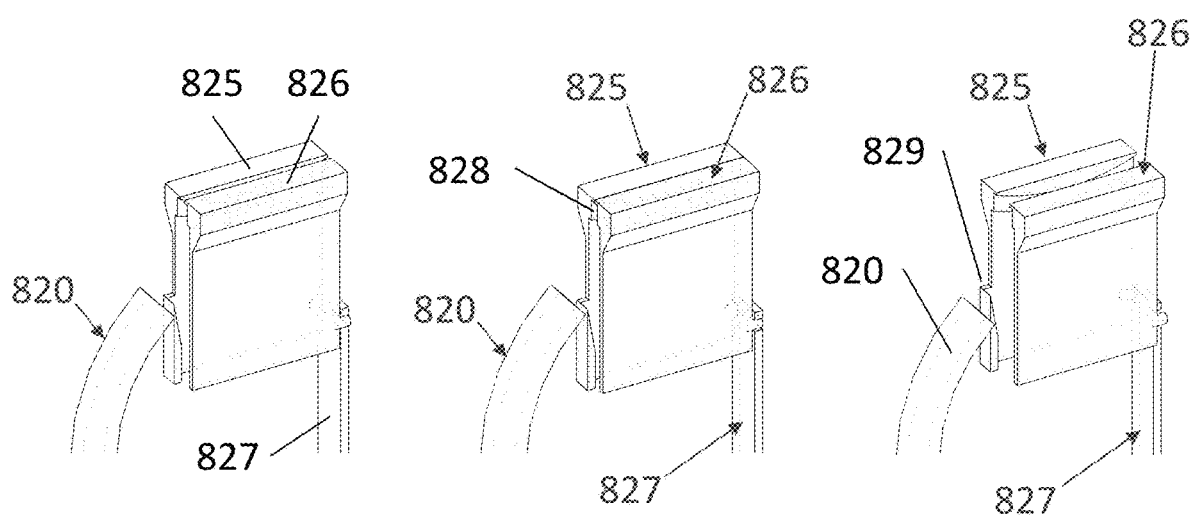

FIGS. 8D, 8E and 8F show detail views of suture grippers 825 and 826. Suture grippers 825 and 826 provide multiple functions in the suture formation process. In an embodiment they are arranged on a ramped guide surface provided on the end effector (not shown in FIGS. 8D, 8E and 8F, but of the sort well known to those skilled in the art of gripping mechanisms) such that they separate as grippers 825 and 826 move distally and come together as they move proximally. Their movement is controlled by flexible gripper actuation linkage 827 which has sufficient flexibility to actuate the grippers throughout the full range of motion of the end effector. The grippers 825 and 826 move into three distinct positions: feed position (FIG. 8D) where the grippers are separated partially to allow suture to pass between them, clamp/weld position (FIG. 8E) where steps 828 in the gripper surfaces come together to clamp and hold the distal end of the suture strand (i.e., the overlapping portions of the suture strand) for loop tensioning and welding, and release/cut position (FIG. 8F) where the grippers separate wide enough to release the welded loop of suture and sharp cutter surface 829 slides distally to snip the welded suture loop free of the suture supply exiting feed tube 820.

FIG. 8C also shows weld electrode 830 actuated distally and proximally by flexible electrode linkage 831 which has sufficient flexibility to control movement of the weld electrode throughout the full range of motion of the end effector.

In an embodiment the suture grippers 825 and 826 are electrically insulated except for the distal surfaces of the grippers contacting the distal side of the overlapping conductive suture segments held in the clamped position. The electrode 830 is electrically insulated except for a portion of the distal surface which can be brought into contact with the proximal side of the overlapping conductive suture segments held in the clamped position. In an embodiment either or both flexible actuation linkages 827 (of grippers 825 and 826) and 831 (of electrode 830) are insulated, and conductive and arranged to deliver electrical energy to either the grippers or the electrode or both. In other embodiments separate flexible insulated wires deliver electrical energy to either or both grippers 825 and 826 and/or electrode 830. In embodiments where only one element (i.e., the grippers 825 and 826, or the electrode 830) has an insulated conductor, the other element (i.e., the electrode 830, or the grippers 825 and 826) may be connected to ground through the instrument shaft and connected components. Electrical potential is applied between the non-insulated portions of the gripper surfaces and the electrode, causing current to flow through the overlapping conductive suture segments, thereby causing localized melting at the interface between the suture segments, resulting in a welded connection between the suture segments. Where the overlapping conductive suture segments are either end of a continuous suture loop, a welded stitch is formed.

FIGS. 9A through 9E illustrate an embodiment of the present invention in a body as it might be viewed by a surgeon at a robotic control console.

Figure 9A:
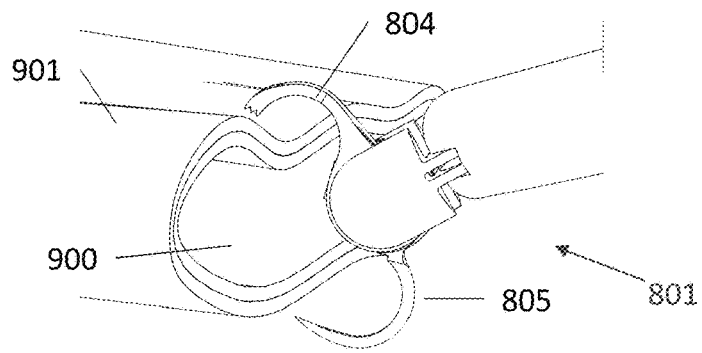
FIGS. 9A-9E are schematic views showing an anatomical closure being effected with the novel end effector shown in FIGS. 8A and 8B.

FIG. 9A shows an opening 900 in tissue 901 that the surgeon would like to close with a stitch. The surgeon's hand and wrist movements at the master-robot on the control console are replicated by the instrument end effector 801 in the body. The surgeon's thumb and forefinger movements are replicated by the tool element 804 and the needle 805. The surgeon positions the tool element 804 and needle 805 astride the tissue opening to be stitched.

Figure 9B:
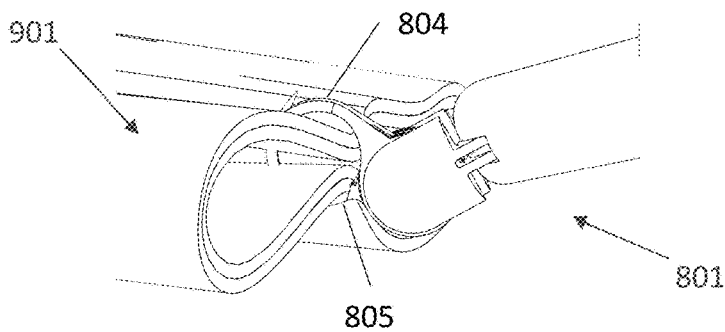

FIG. 9B shows the tool element 804 and needle 805 closed in opposition in response to the surgeon bringing their thumb and forefinger together. The needle 805 has penetrated through both sides of the tissue opening, completing a continuous circular groove (i.e., the conjoined circular grooves 812 and 810) from the needle 805 to the tool element 804. If they are happy with the stitch location defined by the needle placement, the surgeon initiates the stitch process by depressing a footswitch, or a voice-activated command, or other means available to initiate action. In an embodiment the stitch process is a fully automated sequence. In other embodiments some steps are automatically initiated in sequence and others are initiated by the surgeon. The first step in this sequence is activation of a suture advancing mechanism connected to the flexible suture delivery tube 820, which advances a fixed length of conductive suture equal to the circumference of the continuous inward facing groove of the tool element 804 and needle 805 (i.e., the conjoined circular grooves 810 and 812), plus additional material to form an overlapping region for the suture loop. The next step in the sequence is activation of an actuating mechanism connected to the flexible gripper actuation linkage 827 and the suture grippers 825 and 826 to move the grippers from the feed position (FIG. 8D) to the clamp/weld position (FIG. 8E), thereby gripping the distal end of the advanced suture in the overlap region.

Figure 9C:
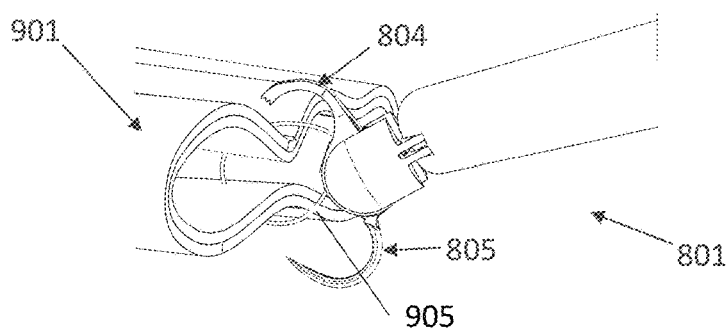

FIG. 9C shows the tool element 804 and needle 805 opened and released from the tissue leaving conductive suture 905 threaded through both sides of the tissue opening.

In an embodiment this motion is controlled by the surgeon at the control console by separation of their thumb and forefinger. In another embodiment, the separation of the tool element 804 and needle 805 is automatically initiated by the robot as part of the automated stitching process.

Figure 9D:
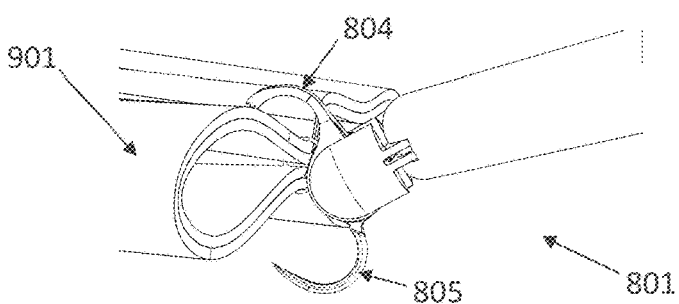

FIG. 9D shows the suture loop tensioned by reversal of the suture advancing mechanism. In an embodiment, tensioning is initiated automatically and suture is pulled to a predetermined or programmed tension value. In another embodiment, the surgeon controls the tensioning process through a control means such as a trigger, slide mechanism, foot switch or similar means. In an embodiment, the control means includes tactile haptic feedback such that the surgeon has the sensation of pulling on the suture to achieve the desired tension of the stitch. In an embodiment where the separation of the tool element 804 and the needle 805 is performed automatically by the robot, the surgeon controls and feels tension through haptic feedback by separation of their thumb and forefinger which is temporarily disengaged from controlling the motion of the tool element 804 and needle 805. Once desired or predetermined tension has been achieved, the weld process is initiated by initiation of an actuator connected to the flexible electrode linkage 831. The electrode 830 is brought into contact with the proximal side of the overlapping region of the conductive suture loop with a predetermined contacting force. Electrical current is then passed through the overlapping region (i.e., by passing an electrical current between electrode 830 and grippers 825 and 826), causing the interface between the suture segments in the overlapping region to locally melt and fuse into a weld.

Figure 9E:
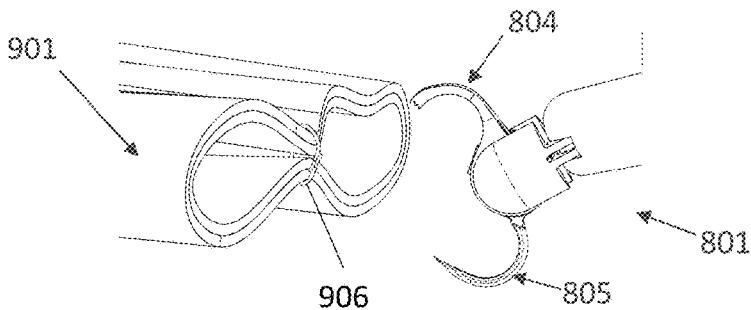

FIG. 9E shows the final step of the stitching sequence where the tensioned, welded loop 906 has been cut free from the suture supply exiting the suture delivery tube 820 and released from the end effector by actuation and movement of the suture grippers 825 and 826 from the clamp/weld position (FIG. 8E) to the cut/release position (FIG. 8F).

Figure 10A:
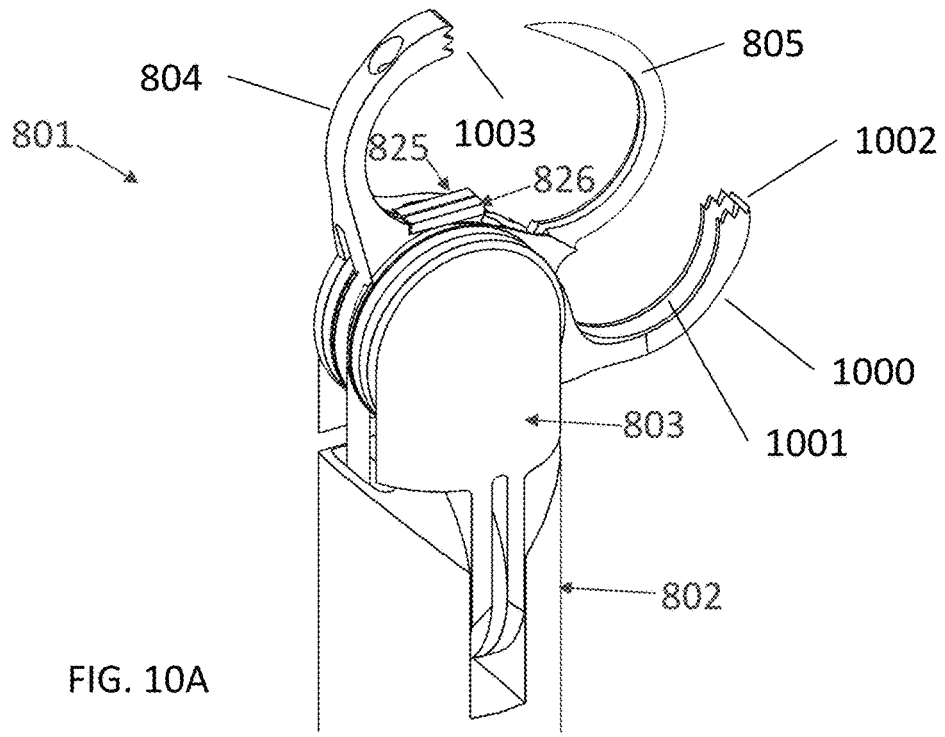
FIG. 10A is a schematic view showing another novel end effector for use in robotic surgery.

FIG. 10A shows an embodiment with integrated tissue grasping and manipulation capability. This embodiment of an end effector has a first tool element 804, a needle 805, and a second opposing hollow tool element 1000. Hollow tool element 1000 includes an opening 1001 which is sufficiently large for needle 805 to rotate through, and a blunt or textured, non-tissue-penetrating end 1002 that directly opposes and aligns with a matching blunt or textured non-tissue-penetrating end 1003 on tool element 804.

FIGS. 10B through 10e show an embodiment of end effector with tissue grasping and manipulation capability (i.e., the end effector of FIG. 10A) as it might be viewed in a body by a surgeon at a robot control console.

Figure 10B:
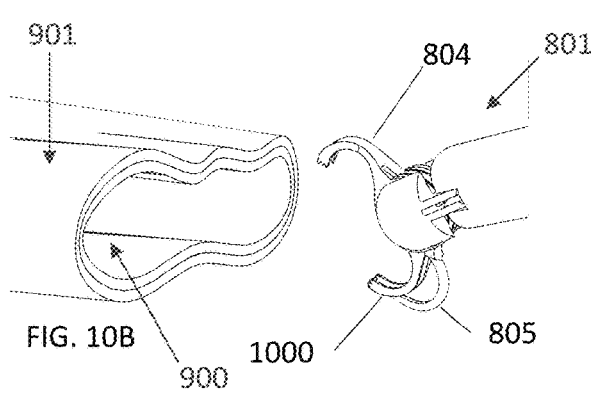
FIGS. 10B-10E are schematic views showing an anatomical closure being effected with the novel end effector shown in FIG. 10A.

FIG. 10B shows first and second opposing tool elements 804 and 1000 separated in preparation for grasping tissue. Needle 805 is outside hollow tool element 1000 and needle point 813 (not shown in FIG. 10B) protected in hollow opening 1001. The motion of the opposing tool elements is controlled by the movement of the surgeon's thumb and forefinger, and needle 804 moves with, and maintains its protected orientation with hollow tool element 1000, while the surgeon grasps and manipulates tissue as one might do with surgical forceps.

Figure 10C:
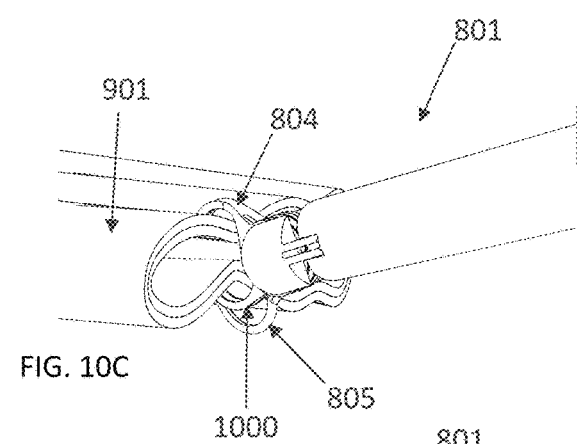

FIG. 10C shows the opposing tool elements 804 and 1000 grasping tissue at a location where the surgeon would like to place a stitch. The non-tissue-penetrating ends of the opposing tool elements 804 and 1000 pinch the tissue at the exact spot where the needle 805 will penetrate, thereby facilitating easy entry and penetration by the needle 805. When satisfied with the location, the surgeon initiates the stitching process by depressing a foot switch, using a voice command or other means to initiate the automated sequence. The first step in the sequence is activation of an actuator that "fires" the needle 805 through the tissue.

Figure 10D:
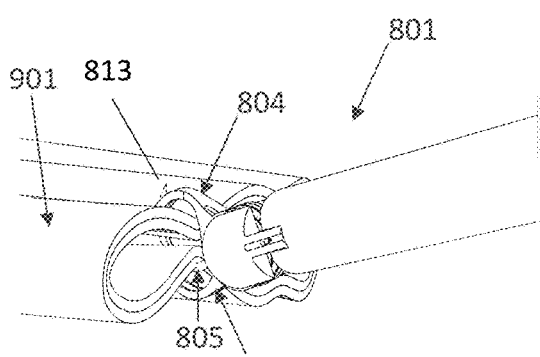

FIG. 10D shows needle point 813 penetrating the tissue and seated in needle hole 811 in tool element 804, and establishing (in conjunction with tool element 804) an uninterrupted suture groove (i.e., the conjoined circular grooves 810 and 812) through the tissue.

Figure 10E:
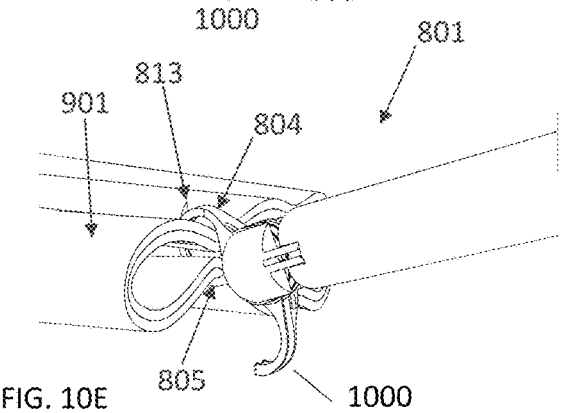

FIG. 10E shows hollow tool element 1000 retracted from the tissue, either by action on the part of the surgeon or automatically as part of the automated stitch sequence, leaving needle 805 in place (i.e., passed through the tissue and seated in needle hole 811 in tool element 804). The remainder of the stitch sequence is the same as that described in FIGS. 9B through 9E.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A device for positioning in a body of an animal, the device comprising a first portion and a second portion positionable in contact with one another, said first portion and said second portion each being a length of suture material comprising a substantially round cross-section, said first portion and said second portion each comprising a biocompatible conductive thermoplastic material, and said first portion and said second portion being disposed substantially parallel to one another, resulting in line contact between said first portion and said second portion, wherein the device is configured such that, when the device is positioned in the body of an animal and electric current flows from said first portion to said second portion, heat is generated by electrical resistance at the line contact between said first portion and said second portion so as to create localized melting of regions of said first portion and said second portion adjacent to the line contact, and the device is configured such that when the electric current is thereafter terminated, the melted regions of said first portion and said second portion re-solidify so that a welded loop of suture is formed between said first portion and said second portion.

2. A device according to claim 1 wherein said biocompatible conductive thermoplastic material comprises a composite of a biocompatible thermoplastic material and a biocompatible conductive material.

3. A device according to claim 2 wherein said biocompatible thermoplastic material comprises a biocompatible thermoplastic polymer, said biocompatible conductive material comprises a biocompatible conductive additive, and further wherein said biocompatible thermoplastic material is formed by compounding said biocompatible thermoplastic polymer with said biocompatible conductive additive.

4. A device according to claim 3 wherein said biocompatible thermoplastic polymer and said biocompatible conductive additive are melt-compounded, extruded and drawn so as to form said lengths of suture material into a monofilament suture.

5. A device according to claim 3 wherein said biocompatible thermoplastic polymer and said biocompatible conductive additive are melt-compounded and molded so as to form said lengths of suture material.

6. A device according to claim 2 wherein said biocompatible thermoplastic material and said biocompatible conductive material are co-extruded and drawn so as to form said lengths of suture material.

7. A device according to claim 2 wherein said biocompatible conductive material is applied as a coating to said biocompatible thermoplastic material.

8. A device according to claim 7 wherein said biocompatible conductive material comprises a pattern of conductive ink applied as a coating to said biocompatible thermoplastic material.

9. A device according to claim 2 wherein said biocompatible thermoplastic material comprises at least one strand of biocompatible thermoplastic polymer, said biocompatible conductive material comprises at least one strand of biocompatible conductive material, and further wherein said biocompatible thermoplastic material is formed by intertwining said at least one strand of biocompatible thermoplastic polymer and said at least one strand of biocompatible conductive material.

10. A device according to claim 2 wherein said biocompatible thermoplastic material comprises a bioabsorbable thermoplastic polymer.

11. A device according to claim 10 wherein said bioabsorbable thermoplastic polymer comprises at least one from the group consisting of polylactic acid (PLA), polyglycolide (PGA), polydioxanone (PDS) and a thermoplastic linear polyester.

12. A device according to claim 2 wherein said biocompatible thermoplastic material comprises a non-absorbable thermoplastic polymer.

13. A device according to claim 12 wherein said non-absorbable thermoplastic polymer comprises at least one from the group consisting of nylon, polypropylene and polycarbonate.

14. A device according to claim 2 wherein said biocompatible conductive material comprises at least one from the group consisting of carbon black, carbon fiber, iron oxide (Fe2O3), a metallic powder and a metallic nanoparticle.

15. A device according to claim 2 wherein said biocompatible conductive material comprises an intrinsically conducting polymer (ICP).

16. A device according to claim 15 wherein said intrinsically conducting polymer (ICP) comprises at least one from the group consisting of polyacetylene, polyaniline, polythiophene and polyphenylenevinylene.

17. A device according to claim 2 wherein said biocompatible thermoplastic material and said biocompatible conductive material are configured so that said biocompatible conductive thermoplastic material provides conductivity in a first direction and prohibits conductivity in a second, different direction.

18. A device according to claim 1 wherein said biocompatible conductive thermoplastic material comprises a biocompatible conductive thermoplastic polymer.

19. A device according to claim 1 wherein said first and second portions are in the form of a continuous length of suture.

20. A method for forming a weld between two portions of a biocompatible conductive thermoplastic material configured to be placed in a body of an animal, wherein the method comprises:
   positioning first and second portions of a biocompatible conductive thermoplastic material in the body of an animal between first and second electrodes so that said first portion is in contact with said first electrode, said second portion is in contact with said second electrode, and said first and second portions of the biocompatible conductive thermoplastic material are in contact with one another, said first portion and said second portion each being a length of suture material comprising a substantially round cross-section, with said first portion and said second portion being disposed substantially parallel to one another, resulting in line contact between said first portion and said second portion;
   applying a selected amount of electrical current across said first and second electrodes so as to generate a selected amount of heat by electric resistance at the line contact between said first and second portions so as to create localized melting of regions of said first and second portions adjacent to the line contact; and
   terminating the electrical current across said first and second electrodes so that the melted regions of said first and second portions re-solidify so that a weld is formed at the line contact.

21. A method according to claim 20 wherein said first and second portions are in the form of a continuous length of suture.

22. A method according to claim 20 wherein formation of a weld at the line contact forms a welded loop of suture.

* * * * *